(12) United States Patent
Sivaguru et al.

(10) Patent No.: US 12,202,806 B2
(45) Date of Patent: Jan. 21, 2025

(54) ECO-FRIENDLY MATERIALS AND METHODS FOR RENEWABLE AND SUSTAINABLE APPLICATIONS IN MATERIAL CHEMISTRY

(71) Applicant: NDSU RESEARCH FOUNDATION, Fargo, ND (US)

(72) Inventors: Jayaraman Sivaguru, Fargo, ND (US); Akila Iyer, Fargo, ND (US); Mukund Sibi, Fargo, ND (US); Dean Webster, Fargo, ND (US); Saravana Kumar Rajendran, Fargo, ND (US); Ramya Raghunathan, Fargo, ND (US); Ravichandanath Singathi, Fargo, ND (US); Retheesh Krishnan, Fargo, ND (US); Anthony Clay, Fargo, ND (US)

(73) Assignee: NDSU RESEARCH FOUNDATION, Fargo, ND (US)

( * ) Notice: Subject to any disclaimer, the term of this patent is extended or adjusted under 35 U.S.C. 154(b) by 459 days.

(21) Appl. No.: 17/248,924

(22) Filed: Feb. 12, 2021

(65) Prior Publication Data
US 2021/0163424 A1 Jun. 3, 2021

Related U.S. Application Data

(63) Continuation of application No. 16/124,418, filed on Sep. 7, 2018, now Pat. No. 10,919,866, which is a continuation of application No. PCT/US2017/021277, filed on Mar. 8, 2017.

(60) Provisional application No. 62/324,189, filed on Apr. 18, 2016, provisional application No. 62/324,194, filed on Apr. 18, 2016, provisional application No. 62/305,044, filed on Mar. 8, 2016.

(51) Int. Cl.
| | |
|---|---|
| C07C 243/28 | (2006.01) |
| C07C 243/30 | (2006.01) |
| C07C 243/34 | (2006.01) |
| C07C 243/38 | (2006.01) |
| C07D 207/24 | (2006.01) |
| C07D 209/48 | (2006.01) |
| C07D 239/88 | (2006.01) |
| C08F 120/14 | (2006.01) |
| C08F 2/48 | (2006.01) |

(52) U.S. Cl.
CPC .......... *C07D 239/88* (2013.01); *C07C 243/28* (2013.01); *C07C 243/30* (2013.01); *C07C 243/34* (2013.01); *C07C 243/38* (2013.01); *C07D 207/24* (2013.01); *C07D 209/48* (2013.01); *C08F 120/14* (2013.01); *C08F 2/48* (2013.01)

(58) Field of Classification Search
CPC ... C07C 243/28; C07C 243/30; C07C 243/34; C07C 243/38; C07D 207/24; C07D 209/48
See application file for complete search history.

(56) References Cited

U.S. PATENT DOCUMENTS

| | | | | |
|---|---|---|---|---|
| 4,530,747 A | * | 7/1985 | Donges | .................. G03F 7/027 522/89 |
| 8,835,558 B2 | | 9/2014 | Lee et al. | |
| 9,738,753 B2 | * | 8/2017 | Sivaguru | ............ C08G 63/6856 |
| 2007/0298516 A1 | | 12/2007 | Hoang et al. | |
| 2014/0275435 A1 | * | 9/2014 | Holmberg | ............. C08F 290/06 525/401 |
| 2015/0105488 A1 | | 4/2015 | Madsen et al. | |
| 2016/0264696 A1 | | 9/2016 | Jeng et al. | |

FOREIGN PATENT DOCUMENTS

| | | |
|---|---|---|
| JP | 2009203401 A | 9/2009 |
| WO | 2012051448 A1 | 4/2012 |

OTHER PUBLICATIONS

Rajendran et al., Programmed Photodegradation of Polymeric/Oligomeric Materials Derived from Renewable Bioresources, Angewandte Chemie, 54, pp. 1159-1163, Published online: Nov. 12, 2014.*
Kurchan, Alexei N. et al., "Dithiane and Trithiane-based Photolabile Molecular Linkers Equipped with Amino-Functionality: Synthesis and Quantum Yields of Fragmentation", Journal of Photochemistry and Photobiology A: Chemistry 171, pp. 121-129. 2005.
NDSU Research Foundation, "The International Search Report and Written Opinion of the International Searching Authority", in connection to PCT/US17/21277 filed Mar. 8, 2017 mailed May 22, 2017.
Abbas et al., "Original and efficient synthesis of 2:1-[α/aza]-oligomer precursors", Tetrahedron Letters, vol. 50, pp. 4158-4160, 2009.
Al-Sehemi, Abdullah, "Synthesis Characterization and Stereostructures of the Pyridazino[6, 1-b]Quinazolinones", UKAU: Sci, vol. 18, pp. 47-62, 2006.
Al-Sehemi et al., "Stereoisomerism in 3-[N-(2-acetoxypropanoyl)-N-acylamino]-quinazolin-4(3H)-ones, enantioselective acylating agents", J. Chem. Soc., Perkin Trans. 1, pp. 4413-4421, 2000.
Al-Sehemi et al., "3-Di-[(S)-2-acetoxypropanoyl]aminoquinazolin-4(3H)-ones: stereostructure and application in kinetic resolution of amines", Tetrahedron Letters, vol. 41, pp. 2243-2246, 2000.

(Continued)

*Primary Examiner* — Bruck Kifle
(74) *Attorney, Agent, or Firm* — McKee, Voorhees & Sease, PLC

(57) ABSTRACT

The invention relates to novel hydrazide-based templates, methods of making the same, and methods of using the hydrazide-based templates as molecular scaffolds for asymmetric light driven transformations, light driven material synthesis, and biological applications. Furthermore, the present invention relates to photoinitiators, monomers, and polymers derived from biomass, together with methods and methods of using the same.

17 Claims, 21 Drawing Sheets

(56) References Cited

OTHER PUBLICATIONS

Al-Sehemi et al., "3-(N,N-Diacylamino)quinazolin-4(3H)-ones as enantioselective acylating agents for amines", Tetrahedron Letters, vol. 41, pp. 2239-2242, 2000.
Anderson et al., "Concepts for ligand design in asymmetric catalysis: a study of chiral amino thiol ligands", Tetrahedron: Asymmetry, vol. 9, pp. 3461-3490, 1998.
Anderson et al., "A Photo-Induced Rearrangement Involving Aryl Participation", Tetrahedron Letters, No. 1, pp. 1-4, 1962.
Aoki et al., "N-Phenylation of N-Arylaminophthalimides with Triphenylbismuth and Cupric Acetate: A Convenient Synthesis of 1-Aryl-1-Phenylhydrazines", Synthetic Communications, www.tandfonline.com/loi/lsyc20, 11 pages, Dec. 4, 2007.
Arthur et al., "Stereostructural behavior of N-N atropisomers: Two conglomerate crystallisations and a crystallisation-induced deracemisation", CrysEngComm, vol. 11, pp. 610-619, Dec. 9, 2008.
Atkinson et al., "Resolution of N-Benzyl-N-(1,2-Dihydro-2-Oxoquinolin-1-YL)Glycine", Tetrahedron Letters, No. 41, pp. 4001-4002, 1979.
Atkinson et al., "Rotational Isomerism in N-(N-Heteroaryl)arenesulphenamides", J. Chem. Soc. Perkin Trans. 2, pp. 1490-1495, Jan. 1, 1979.
Atkinson et al., "The N—N Bond as a Chiral Axis: 3-(Diacylamino)quinazolin-4(3H)ones as Chiral Acylating Agents", J. Chem. Soc., Chem. Commun., pp. 1159-1160, Jan. 1, 1994.
Atkinson et al., "Completely diastereoselective aziridination of α,β-unsaturated acids via intramolecular reaction of 3-acetoxyaminoquinazolin-4(3H)-ones", Tetrahedron Letters, vol. 43, pp. 2083-2085, 2002.
Auvergne et al., "Biobased Thermosetting Epoxy: Present and Future", Chem. Rev., vol. 114, pp. 1082-1115, 2014.
Barsotti et al., "Photochemical processes induced by the irradiation of 4-hydroxybenzophenone in different solvents", Photochem. Photobiol. Sci., vol. 14, pp. 2087-2096, 2015.
Besson et al., "Conversion of Biomass into Chemicals over Metal Catalysts", Chem. Rev., vol. 114, pp. 1827-1870, 2014.
Bishop et al., "Torsional Barriers in NN'-Diacylhydrazines", Chemical Communications, pp. 672-674, Jan. 1, 1967.
Bourel et al., "Improved Synthesis of Pyridazinediones Under Microwave Irradiation", Tetrahedron Letters, vol. 37, No. 24, pp. 4145-4148, 1996.
Brosse et al., "A New Synthetic Route to Protected α-Hydrazinoesters in High Optical Purity Using the Mitsunobu Protocol", J. Org. Chem., vol. 66, pp. 2869-2873, 2001.
Chatani et al., "The power of light in polymer science: photochemical processes to manipulate polymer formation, structure, and properties", Polym. Chem., vol. 5, pp. 2187-2201, 2014.
Chan, Dominic, "Promotion of Reaction of N—H Bonds with Triarylbismuth and Cupric Acetate", Tetrahedron Letters, vol. 37, No. 50, pp. 9013-9016, 1996.
Conley et al., "A New Synthetic Route to Authentic N-Substituted Aminomaleimides", J. Org. Chem., vol. 70, pp. 4553-4555, 2005.
Coogan et al., "Synthesis of unsymmetrical 3,3'-biquinazoline-2,2'-diones by condensation of 3-aminoquinazolinones with benzoxazinones; fortuitous discovery, and further syntheses of 4-H-3-oxo-1,9a,10-triazaanthracen-9-ones", Org. Biomol. Chem., vol. 3, pp. 1134-1139, 2005.
Coogan et al., "Tetraacyl hydrazines and 3,3'-biquinazoline-4,4'-diones; synthesis, studies of rotational barriers and deracemisation", J. Chem. Soc., Perkin Trans. 2, pp. 2060-2066, 2000.
D'Acquarica et al., "Dynamic HPLC on chiral stationary phases: A powerful tool for the investigation of stereomutation processes", J. Sep. Sci., vol. 29, pp. 1508-1516, 2006.
Draghici, Cristian, "Discovery of a Novel Ring Fragmentation Reaction; Efficient Preparation of Tethered Aldehyde Ynoates and N-Containing Heterocycles; Radical Addition Approach to Asymmetric Amine Synthesis", A Dissertation Presented to the Faculty of the Graduate College of the University of Vermont, 307 pages, Oct. 2, 2009.

Fletcher et al., "Conformational Changes in Tetra-alkylhydrazines", Chemical Communications, 706-708, Jan. 1, 1969.
Gandini et al., "The Furan Counterpart of Poly(ethylene terephthalate): An Alternative Material Based on Renewable Resources", Journal of Polymer Science: Part A: Polymer Chemistry, vol. 47, pp. 295-298, 2008.
Givens et al., "Applications of p-hydroxyphenacyl (pHP) and coumarin-4-ylmethyl photoremovable protecting groups", Photochem. Photobiol. Sci., vol. 11, pp. 472-488, 2012.
Gomes et al., "Synthesis and Characterization of Poly(2,5-furan dicarboxylate)s Based on a Variety of Diols", Journal of Polymer Science Part A: Polymer Chemistry, vol. 49, pp. 3759-3768, 2011.
Guardado-Alvarez et al., "Nanovalve activation by surface-attached photoacids", Chem. Commun. vol. 50, pp. 8388-8390, 2014.
Harmsen et al., "Green building blocks for biobased plastics; biobased processes and market development", Wageningen UR, 79 pages, Jan. 2013.
Hynes, Jr et al., "N-Amination of Pyrrole and Indole Heterocycles with Monochloramine (NH2Cl)", J. Org. Chem., vol. 69, pp. 1368-1371, 2004.
Iwata et al., "Photo-induced glycosylation using reusable organophotoacids", Chem. Commun., vol. 50, pp. 10695-10698, 2014.
Jin et al., "Alcohols as alkylating agents in heteroarene C—H functionalization", Nature, vol. 525, pp. 87-90, Sep. 3, 2015.
Kaminski et al., "Design, synthesis, and anticonvulsant activity of N-phenylamino derivatives of 3,3-dialkyl-pyrrolidine-2,5-diones and hexahydro-isoindole-1,3-diones", Bioorganic & Medicinal Chemistry, vol. 16, pp. 4921-4931, 2008.
Karton-Lifshin et al., ""Donor-Two-Acceptor" Dye Design: A Distinct Gateway to NIR Fluorescence", J. Am. Chem. Soc., vol. 134, pp. 20412-20420, 2012.
Keitz et al., "A Tandem Approach to Photoactivated Olefin Metathesis: Combining a Photoacid Generator with an Acid Activated Catalyst", J. Am. Chem. Soc., vol. 131, pp. 2038-2039, 2009.
Kim et al., "Use of N—N Bond Stereodynamics in Ring-Closing Metathesis to Form Medium-Sized Rings and Macrocycles", Organic Letters, vol. 6, No. 23, pp. 4351-4353, 2004.
Korsch et al., "Restricted Rotation About N—N Single Bonds, The Conformation of Tetrahydropyridazine Rings", Tetrahedron Letters, No. 47, pp. 5897-5903, 1966.
Kumasaka et al., "Photoexcited States of UV Absorbers, Benzophenone Derivatives", Photochemistry and Photobiology, vol. 90, pp. 727-733, 2014.
Lim et al., "Novel Route to Azobenzenes via Pd-Catalyzed Coupling Reactions of Ayl Hydrazides with Aryl Halides, Followed by Direct Oxidations", Organic Letters, vol. 5, No. 7, pp. 979-982, 2002.
Moreau et al., "Recent catalytic advances in the chemistry of substituted furans from carbohydrates and in the ensuing polymers", Topics in Catalysis, vol. 27. Nos. 1-4, pp. 11-30, Feb. 2004.
Moriarty et al., "Conformational Studies on the Amido Group, Hindered Internal Rotation in N,N1-Dialkyl Hydrazocarboxylates", Tetrahedron Letters, No. 17, pp. 1603-1609, 1967.
Ottersbach et al., "Induction of chirality: experimental evidence of atropisomerism in azapeptides", Chem. Commun., vol. 48, pp. 5772-5774, 2012.
Palit, Dipak, "Photophysics and excited state relaxation dynamics of p-hydroxy and p-amino-substituted benzophenones: a review" Res. Chem. Intermed., vol. 31, No. 1-3, pp. 205-225, 2005.
Prasad Hari et al., "The Photoredox-Catalyzed Meerwein Addition Reaction: Intermolecular Amino-Arylation of Alkenes", Angew. Chem. Int. Ed., vol. 53, pp. 725-728, 2014.
Rajendran et al., "Programmed Photodegradation of Polymeric/Oligomeric Materials Derived from Renewable Bioresources", Angew. Chem. Int. Ed., vol. 54, pp. 1159-1163, 2015.
Reijenga et al., "Development of Methods for the Determination of $pK_a$ Values" Analytical Chemistry Insights, vol. 8, pp. 53-71, 2013.
Rosatella et al., "5-Hydroxymethylfurfural (HMF) as a building block platform: Biological properties, synthesis and synthetic applications", Green Chem., vol. 13, pp. 754-793, 2011.
Rosen et al., "Total Synthesis of Dixiamycin B by Electrochemical Oxidation", J. Am. Chem. Soc., vol. 136, pp. 5571-5574, 2014.

(56) References Cited

OTHER PUBLICATIONS

Schneider et al., "Effect of co-initiator ratio on the polymer properties of experimental resin composites formulated with camphorquinone and phenyl-propanedione", Dental Materials, vol. 25, pp. 369-375, 2009.
Shen et al., "Comparison of Electrophilic Amination Reagents for N-Amination of 2-Oxazolidinones and Application to Synthesis of Chiral Hydrazones", J. Org. Chem. vol. 67, pp. 6236-6239, 2002.
Shirai et al., "Photoacid and Photobase Generators: Prospects and Their use in the Development of Polymeric Photosensitive Systems", Bull. Chem. Soc. Jpn., vol. 71, pp. 2483-2507, 1998.
Simkovitch et al., "Comparison of the rate of excited-state proton transfer from photoacids to alcohols and water", Journal of Photochemistry and Photobiology A: Chemistry, vol. 277, pp. 90-101, 2014.
Sunal et al., "Monoamine oxidase inhibitory activities of novel 3,4-dihydroquinolin-(1H)-2-one derivatives", J Neural Transm., vol. 114, pp. 717-719, 2007.
Tehfe et al., "Photopolymerization Reactions: On the Way to a Green and Sustainable Chemistry", Appl. Sci., vol. 3, pp. 490-514, 2013.
Tolbert et al., "Photoexcited Proton Transfer from Enhanced Photoacids", J. Am. Chem. Soc., vol. 116, pp. 10593-10600, 1994.
Torti et al., "Aryl tosylates as non-ionic photoacid generators (PAGs): photochemistry and applications in cationic photopolymerizations", RSC Adv., vol. 5, pp. 33239-33248, 2015.
Trapp, Oliver, "Interconversion of Stereochemically Labile Enantiomers (Enantiomerization)", Topics in Current Chemistry, vol. 341, pp. 231-269, 2013.
Tšubrik et al., "Arylation of Diversely substituted hydrazines by tri- and pentavalent organobismuth reagents", Tetrahedron, vol. 60, pp. 8363-8373, 2004.
Van Putten et al., "Hydroxymethylfurfural, A Versatile Platform Chemical Made from Renewable Resources", Chem. Rev., vol. 113, pp. 1499-1597, 2013.
Verma et al., "Conformational Analysis about the Nitrogen-Nitrogen' Bond by Nuclear Magnetic Resonance Spectroscopy. N'-Sulfonyl Derivatives of N-Aminocamphorimide", J. Org. Chem., vol. 38, No. 21, pp. 3745-3749, 1973.
Verma et al., "Conformational Analysis by Nuclear Magnetic Resonance Spectroscopy. N'Derivatives of N-Aminocamphorimides", J. Org. Chem., vol. 38, No. 5, pp. 1004-1010, 1973.
Verma et al., "Conformational Analysis About N—N Bond by NMR Spectroscopy:N'-Sulphonyl Derivatives of N-Aminoimides of Anthracene-Citraconic Anhydride and Naphthalene-Maleic Anhydride Adducts", Bulletin of the Chemical Society of Japan, vol. 47, No. 9, pp. 2311-2314, Sep. 1974.
Verma et al., "Studies on N, N'-Diimidyl Systems by Nuclear Magnetic Resonance Spectroscopy", Can J. Chem., vol. 52, pp. 2399-2402, 1974.
Verma et al., "Structural Assignment by NMR Analyses of N-(Diacylamino)imide Derivatives. Diels-Alder Adducts of 2,3-Dimethylnaphthalene and 6,6-Diphenylfulvene with Maleic Anhydride", Bulletin of the Chemical Society of Japan, vol. 51, No. 2, pp. 516-519, 1978.
Verma et al., "Structural Assignment by NMR Spectroscopy: Restricted Rotation about Aryl C—N Bond and Configurations of Diels-Alder Adducts", Bulletin of the Chemical Society of Japan, vol. 51. No. 2, pp. 520-523, 1978.
Yang et al., "Synthesis and photopolymerization kinetics of benzophenone sesamol one-component photoinitiator", Photochem Photobiol. Sci., vol. 12, pp. 323-329, 2013.
Yao et al., "Controlled Polymerization of Next-Generation Renewable Monomers and Beyond", Macromolecules, vol. 46, pp. 1689-1712, 2013.
Sudha et al., "A convenient preparation of novel benzophenone derivatives", J. Serb. Chem. Soc., vol. 73., No. 3, pp. 261-270, 2008.
Il'Ichev et al., "Photochemical Reaction Mechanisms of 2-Nitrobenzyl Compounds: Methyl Ethers and Caged ATP", J. Am. Chem. Soc., vol. 126, pp. 4581-4595, 2004.
English Translation by WIPO of JP 2009-203401-A, 13 pages, (2009).

* cited by examiner

ECO-FRIENDLY MATERIALS AND METHODS FOR RENEWABLE AND SUSTAINABLE APPLICATIONS IN MATERIAL CHEMISTRY

CROSS-REFERENCE TO RELATED APPLICATIONS

This application is a divisional of U.S. patent application Ser. No. 16/124,418, filed Sep. 7, 2018, which is a continuation of PCT/US2017/21277, filed Mar. 8, 2017, which claims priority under 35 U.S.C § 119 to Provisional Patent Application Ser. No. 62/305,044 filed Mar. 8, 2016, Provisional Patent Application Ser. No. 62/324,194 filed Apr. 18, 2016, and Provisional Patent Application Serial No. 62/324, 189 filed Apr. 18, 2016, herein incorporated by reference in their entirety.

STATEMENT AS TO FEDERALLY FUNDED RESEARCH

This invention was made with government support under Contract No. 1465075 awarded by the National Science Foundation (NSF), and by the National Science EPSCOR (EPS IIA-1355466) for the Center for Sustainable Materials Science (CSMS), North Dakota State University, Fargo, ND, USA. The government has certain rights in the invention.

FIELD OF THE INVENTION

The invention relates to biobased, sustainable and renewable polymers. In some aspects, the polymers are photodegradable. In some aspects, novel hydrazide-based templates, methods of making the same, and methods of using the hydrazide-based templates as molecular scaffolds for asymmetric light driven transformations, light driven material synthesis, and biological applications.

BACKGROUND OF THE INVENTIONS

Coal, oil and natural gas form part of the fossil fuels that are used for power generation, fuels in transportation, energy supply as well as feed stock chemicals in the synthesis of polymers, medicine, textiles, paints, etc. With the constant depletion of fossil fuels, and the increased demand of polymers, worldwide efforts have been devoted towards identifying renewable and sustainable methods and materials. Therefore, it is a primary object, feature, or advantage of the present invention to improve upon the state of the art. It is an additional object, feature, or advantage of the present invention to use biomass as a conduit to renewable and sustainable polymers and in methods of making the same.

Biomass not only gives a greener alternative to fossil fuels but also is an inexpensive option that is abundant in nature and most importantly is renewable[1]. Many important intermediates can be derived from carbohydrates, glucose or fructose, including hydroxymethylfurfural (HMF), and 2,5-Furandicarboxylic acid (FDCA) which are listed among the top 14 biobased chemicalsla. FDCA, which is structurally similar to Terephthalic acid, have been used as a replacement in the synthesis of polyethylene terephthalate (PET). Gandini and coworkers have extensively studied the synthesis and characterization of polymers produced with FDCA as the monomer[2]. While these materials are made from renewable resources, after their usage they are discarded and contribute to landfill mass. Therefore, it is an additional object, feature, or advantage of the present invention to provide controlled photodegradable polymers derived from renewable resources. It is another object, feature, or advantage of the present invention to provide a photodegradable polymer with nitrobenzyl photo trigger unit in its backbone.

o-Nitrobenzyl derivative is one of the most commonly used phototriggers and its mechanism of action are well established in the literature, however the release of the leaving group is in the microseconds time[4] and the formation of o-nitroso derivative as a byproduct during the cleavage process represent significant drawbacks. The o-nitroso derivative absorbs more of the irradiation wavelength (~350 nm) than the parent compound, thus this competitive absorption of the product interferes with the release of the leaving group[5]. In addition, it is believed that the formation of o-nitroso derivative interacts with the cleaved FDCA monomer thereby reducing its recovery. In one object, feature, or advantage of the invention alleviates the challenges associated with o-nitrobenzyl derivative by providing phenacyl compounds as a phototrigger.

Photoinitiators have been used for various applications including, polymerization, photocuring and device fabrication[6]. These include photoinitiators that are employed for free radical polymerization, which can be classified into two types; Type-I (e.g. radicals formed cleavage reaction) and Type-II (e.g. radicals formed abstraction reaction). Free radical polymerization reactions have found various applications in coatings, printing inks, adhesives and photoresists[7].

Free radical photoinitiators have light absorbing units at suitable wavelength to produce reactive species (e.g. radical pair), which in turn reacts with monomers thus initiating the polymerization. Amongst these benzophenone and other Type-II photoinitiators have been employed with several different co-initiators which aid in photochemical polymerization[8-12]. Over the past few decades benzophenone has been synthesized and investigated for its ability to afford polymeric materials[10].

The mechanistic pathway involved for photochemical polymerization of benzopenone photoinitiators is hydrogen abstraction, wherein an available hydrogen with appropriate bond dissociation energy is abstracted from a suitable donor (co-initiator), forming a ketyl radical of the photoinitiator and radical of the co-initiator. Photochemical polymerization via Type-II photoinitiators goes via step growth polymerization. The radical of the co-initiator is most commonly the radical, which begins the propagation process. However, studies have shown that the photoinitiator can also commence propagation. The co-initiator then becomes a part of the polymer due to trapping, and radical addition the photoinitiator also can become a part of the polymeric material. Thus, changing the photoinitiator of co-initiator can change the morphology and polymeric properties. The dependence of the polymerization on the co-initiator employed has been well studied in the literature. Commonly employed co-initiators include amines, alcohols, thiols and secondary alkanes. The photophysical properties of various benzophenone derivatives has also been investigated. A union of the two studies shows the dependence of polymerization on the co-initiator employed corroborated by photophysical investigations allows for strengthened polymer properties aided by judicious co-initiator selection.

A third, Type-III photoinitiator is an acid or base polymerization. These govern innumerable processes in our daily life, from cellular activity on the micro scale to day to day cleaning and hygiene on the macro scale. The photoacid generation derived from biomass have lower excited state pKa's hence act as an excellent acid upon interaction with light.

Lastly, traditional photoreactions that work under ultraviolet (UV) light have been utilized to synthesize complex structural scaffolds and to build materials and molecular assemblies with unique architectures. Most often, UV light is used to effect photochemical change as shorter wavelength light (200 to 400 nm) is more energetic (150 to 70 kcal/mole) than longer wavelength (400 to 800 nm) visible light (70 to 40 kcal/mole). However, there remains a need to provide an alternative environmentally friendly strategy to initiate photoreactions that do not rely on the UV spectrum.

Developing a general strategy to initiate excited state reactions using visible light to preform photoreactions has presented challenges. Most organic compounds are transparent to visible light and their excited state energy is high. Overcoming the high-energy state requires UVA/UVB light absorption for initiating photochemical transformations. Furthermore, traditional photoreactions that are known to be useful for generating complex structures cannot be imitated using this strategy as the reaction does not originate from the excited state. Accordingly, there remains a long-standing need to develop a general strategy for photoreactions with visible light that is applicable to a wide variety of reactions. Consequently, one object, feature, or advantage of the invention provides hydrazide-based templates, methods of making the same, and methods of using the hydrazide-based templates as molecular scaffolds for asymmetric light driven transformations, light driven material synthesis, and biological applications.

BRIEF DESCRIPTION OF THE INVENTION

In one aspect, novel photodegradable polymers derived from biomass are provided, together with methods of making and methods of using said polymers. In one aspect, the photodegradable polymer contains at least one first monomeric unit comprising a monomer obtained from biomass and at least one second monomeric unit comprising a phototrigger. Optionally, the photodegradable polymer can contain a plurality of first monomeric units, each one obtained from biomass. Optionally, the photodegradable polymer can contain a plurality of phototrigger monomeric units, which can be selected to photocleave at the same or different wavelengths. Optionally, the photodegradable polymer further includes at least one third monomeric unit, wherein the third monomeric unit is obtained from a petroleum product or is chemically or enzymatically synthesized. The optional third monomeric unit can be, for example, a hydrophilic monomer, such as an alkylene glycol. In some embodiments, the photodegradable polymer can contain a greater number of first monomeric units than second monomeric units. In some embodiments of the photodegradable polymer containing one or more optional third monomeric units, the polymer can contain greater numbers of first and/or third monomeric units compared to the number of second monomeric units.

In one aspect of the invention, novel methods of making and using the photodegradable polymers, as well as methods for making and using or reusing photodegradation products of the photodegradable polymers, are also provided. In one aspect, the method for making the photodegradable polymer includes reacting a bifunctionalized first monomeric unit with a bifunctionalized second monomeric unit under conditions and for a time to yield the photodegradable polymer. Optionally, the method can further include reacting a bifunctionalized third monomeric unit with said first and second monomeric units to yield the photodegradable polymer.

In another aspect, a method is provided for recycling a photodegradable polymer. The method can include photodegrading the photodegradable polymer to yield one or more degradation products that include one or more recycled monomers or oligomers. An exemplary method for degrading the photodegradable polymer includes exposing the polymer to light having a wavelength selected to cause photocleavage of the polymer, under conditions and for a time sufficient to yield the recycled monomers or oligomers.

Optionally, at least one of the recycled monomers or oligomers can be used to synthesize a polymer comprising the recycled monomer or oligomer. A recycled monomer or oligomer of interest can be optionally isolated, separated or purified from other products of photo degradation of the polymer. The recycled monomer or oligomer can optionally be stored and/or transported prior to being used in further methods for polymer synthesis.

Polymers and oligomers that contain at least one recycled monomer or oligomer as described herein are also encompassed by the invention.

DETAILED DESCRIPTION OF THE INVENTION

Figure 1:
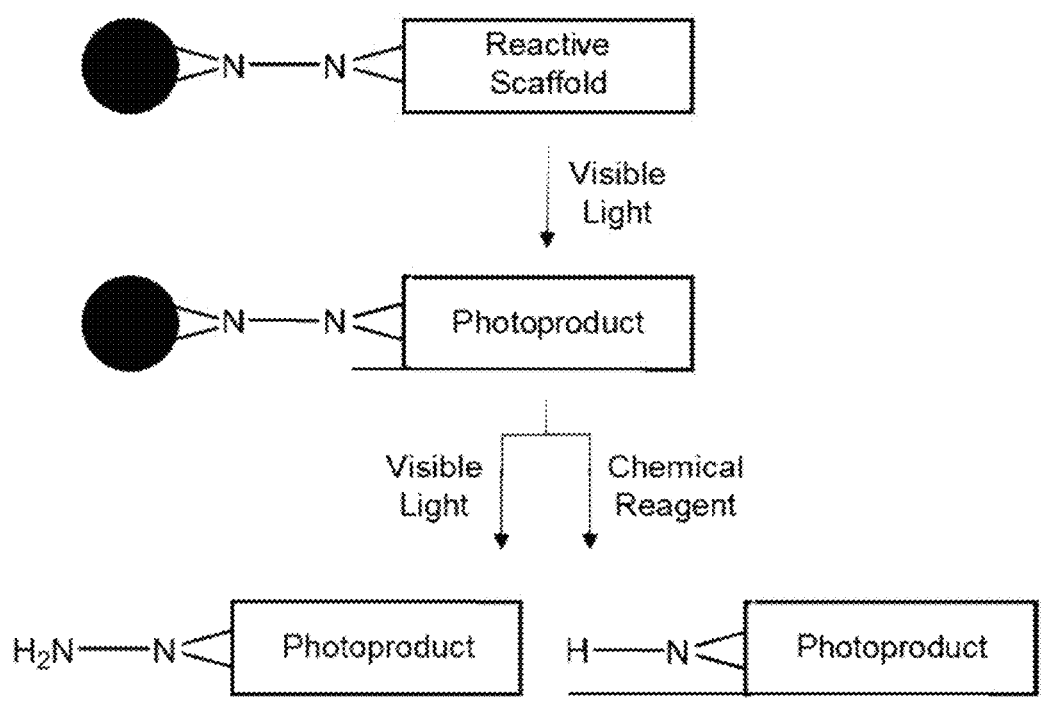
FIG. 1 shows a working paradigm for the hydrazide derivatives undergoing visible light mediated transformations.

It is to be understood that all terminology used herein is for the purpose of describing particular embodiments only, and is not intended to be limiting in any manner or scope. For example, as used herein the singular forms "a," "an" and "the" can include plural referents unless the content clearly indicates otherwise. Additionally, all units, prefixes, and symbols may be denoted in its SI accepted form.

Numeric ranges recited within the specification are inclusive of the numbers defining the range and include each integer and fraction within the defined range. Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible sub-ranges, fractions, and individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6, and decimals and fractions, for example, 1.2, 3.8, 1½, and 4¾ This applies regardless of the breadth of the range.

The term "about," as used herein, refers to variation in the numerical quantity that can occur, for example, through typical measuring techniques and equipment, with respect to any quantifiable variable, including, but not limited to, mass, volume, time, distance, wave length, and frequency. Further, given solid and liquid handling procedures used in the real world, there is certain inadvertent error and variation that is likely through differences in the manufacture, source, or purity of the ingredients used to make the compositions or carry out the methods and the like. The term "about" also encompasses these variations. Whether or not modified by the term "about," the claims include equivalents to the quantities.

As used herein, "optional" or "optionally" means that the subsequently described event or circumstance does or does not occur and that the description includes instances where said event or circumstance occurs and instances where it does not. For example, an optionally variant portion means that the portion is variant or non-variant.

It should be understood that the term "polymer" is inclusive of compounds known as oligomers, polymers, homopolymers, heteropolymers and copolymers, without limitation. In some embodiments, the polymers of the invention include at least one first monomeric unit derived from biomass, and at least one second monomeric unit that constitutes a phototrigger.

In one aspect, the photodegradable polymer contains at least one first monomeric unit comprising a monomer obtained from biomass and at least one second monomeric unit comprising a phototrigger.

As used herein, the term "alkyl" or "alkyl group" refers to saturated hydrocarbons having one or more carbon atoms, including straight-chain alkyl groups (e.g., methyl, ethyl, propyl, butyl, pentyl, hexyl, heptyl, octyl, nonyl, decyl, etc.), cyclic alkyl groups (or "cycloalkyl" or "alicyclic" or "carbocyclic" groups) (e.g., cyclopropyl, cyclopentyl, cyclohexyl, cycloheptyl, cyclooctyl, etc.), branched-chain alkyl groups (e.g., isopropyl, tert-butyl, sec-butyl, isobutyl, etc.), and alkyl-substituted alkyl groups (e.g., alkyl-substituted cycloalkyl groups and cycloalkyl-substituted alkyl groups).

Unless otherwise specified, the term "alkyl" includes both "unsubstituted alkyls" and "substituted alkyls." As used herein, the term "substituted alkyls" refers to alkyl groups having substituents replacing one or more hydrogens on one or more carbons of the hydrocarbon backbone. Such substituents may include, for example, alkenyl, alkynyl, halogeno, hydroxyl, alkylcarbonyloxy, arylcarbonyloxy, alkoxycarbonyloxy, aryloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), imino, sulfhydryl, alkylthio, arylthio, thiocarboxylate, sulfates, alkylsulfinyl, sulfonates, sulfamoyl, sulfonamido, nitro, trifluoromethyl, cyano, azido, heterocyclic, alkylaryl, or aromatic (including heteroaromatic) groups.

In some embodiments, substituted alkyls can include a heterocyclic group. As used herein, the term "heterocyclic group" includes closed ring structures analogous to carbocyclic groups in which one or more of the carbon atoms in the ring is an element other than carbon, for example, nitrogen, sulfur or oxygen. Heterocyclic groups may be saturated or unsaturated. Exemplary heterocyclic groups include, but are not limited to, aziridine, ethylene oxide (epoxides, oxiranes), thiirane (episulfides), dioxirane, azetidine, oxetane, thietane, dioxetane, dithietane, dithiete, azolidine, pyrrolidine, pyrroline, oxolane, dihydrofuran, and furan.

In some embodiments, the invention relates to curable coating compositions which may be formulated with or without solvents. A curable coating composition of the invention contains a resin such as those discussed above, and optionally one or more solvents. A coating composition may be a solvent-free coating composition or may optionally contain a solvent such as, for example, acetone, THF, methyl ethyl ketone (MEK), xylene, etc. The coating composition may be a solution in such a solvent or mixture of solvents. The invention also relates to the use of a coating composition which may be coated onto a substrate and cured using techniques known in the art. The substrate can be any common substrate such as paper, polyester films such as polyethylene and polypropylene, metals such as aluminum and steel, glass, urethane elastomers, primed (painted) substrates, and the like. The coating composition of the invention may be cured at room temperature (ambient cure) or at elevated temperatures (thermal cure). A coating composition of the invention may further contain coating additives. Examples of such coating additives include, but are not limited to, one or more leveling, rheology, and flow control agents such as silicones, fluorocarbons or cellulosics; extenders; reactive coalescing aids such as those described in U.S. Pat. No. 5,349,026, incorporated herein by reference; plasticizers; flatting agents; pigment wetting and dispersing agents and surfactants; ultraviolet (UV) absorbers; UV light stabilizers; tinting pigments; colorants; defoaming and antifoaming agents; anti-settling, anti-sag and bodying agents; anti-skinning agents; anti-flooding and anti-floating agents; biocides, fungicides and mildewcides; corrosion inhibitors; thickening agents; or coalescing agents. Specific examples of such additives can be found in Raw Materials Index, published by the National Paint & Coatings Association, 1500 Rhode Island Avenue, N.W., Washington, D.C. 20005. Further examples of such additives may be found in U.S. Pat. No. 5,371,148, incorporated herein by reference As used herein, the terms "UV light" and "ultraviolet light" refer to the portion of the electromagnetic spectrum having a wavelength of about 100 nm and about 390 nm.

As used herein, the term "visible light" refers to the portion of the electromagnetic spectrum typically considered visible to the human eye. This typically includes the wavelengths between about 390 nm and 700 nm, or a frequency between about 430 THz and about 770 THz.

A suitable wavelength of light that can be used in some embodiments of the present invention is generally in the visible range. Preferably, the wavelength is from about 250 nm to about 700 nm, more preferably from about 250 nm to about 530 nm, more preferably from about 300 nm to about 450 nm, most preferably about 300 nm. Each range of wavelengths includes all integer wavelengths in the range.

Hydrazide-Derived Compounds

Molecular scaffolds are prepared based on a hydrazide-derived compound. Hydrazides are a class of organic compounds that comprise a functional group characterized by a nitrogen to nitrogen covalent bond and having four substituents, wherein at least one of the substituents is an acyl group. The hydrazide framework is versatile and can be functionalized to provide a template for the formation of desired compounds. The general structure of a hydrazide is:

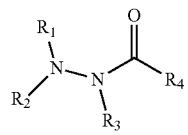

Where $R_1$, $R_2$, $R_3$, and $R_4$, can be a hydrogen, a halide, an organic functional group, or inorganic functional group. One of the R groups is a photoreactive group that is photoreactive to visible light. Non-limiting examples of suitable organic functional groups include, but are not limited to, an acid anhydride, an alcohol, an aldehyde, an alkane, an alkene, an alkyl, an alkyne, an amide, an amine, an arene, an azo compound, a cabamate, a carboxylic acid, an ether, an epoxide, an ester, an imine, an isocyanate, a ketone, a nitrile, a thiol, derivatives thereof, or combinations thereof. Non-limiting examples of suitable inorganic functional groups include, but are not limited to, those containing actinides, alkali metals, alkaline metals, metalloids, lanthanides, nitrogen-containing compounds such as nitrates and nitrites, phosphorus-containing compounds such as phosphates and phosphites, sulfur containing compounds such as sulfates, sulfites, and sulfonates, transition metals, derivatives thereof, and combinations thereof. In a preferred embodiment, at least one of $R_1$, $R_2$, $R_3$, and $R_4$ comprises a thiol group or a thiol-based derivative.

The hydrazide-derived compound can be prepared from a hydrazine precursor by the addition of an acyl group to the hydrazine compound.

The hydrazide-based compounds can be prepared as a molecular scaffold to enable the scaffold to serve as a template for the formation of a desired compound or tagging of a compound with a functional group from the hydrazide-based scaffold.

Visible Light Mediated Chemical Transformations

Per methods of the invention a hydrazide-based compound is formed into a molecular scaffold. The hydrazide-based compounds can be synthesized and/or functionalized as desired, or purchased with the desired functional substituents. The hydrazide derived scaffold can serve as a template for visible light mediated chemical transformations. UV light mediated chemical transformations have previously been accomplished for certain compounds; however, such transformations were not previously capable using visible light. The methods of the present invention, make visible light mediated chemical transformations possible in addition to UV mediated chemical transformations. Thus, in preferred methods the chemical transformations occur via visible light. And in certain embodiments of the invention, there is no need for UV light mediated chemical transformations, only visible light.

Photocatalysis has recently gained a lot of attention among the researchers due to its ability to provide an alternative green strategy in comparison to the thermal methodologies.[1,2] In this regards, Applicant's work was focused on developing a methodology that utilizes metal free visible light photocatalysis that is not based on photoredox chemistry. Novel scaffold design allows us to perform visible light mediated traditional photochemistry viz. [2+2]-photocycloaddition, Paternò-Büchi reaction, 6π photocyclization and Norrish-Yang reaction with high yields in the photoproduct. This is an unusual finding in the sense that performing classical photoreactions using visible light has not been studied so far in the literature. The present photochemical strategy showcases a diverse range of compounds that can undergo photoreaction smoothly to afford products followed by recovering the scaffold. As set forth in the Examples, detailed photophysical experiments were performed which corroborates the experimental findings and highlights the role of excited state reactivity of these novel scaffolds. Further, the work shown here within demonstrates these scaffolds to be the first-of-a-kind chiral molecules that are stable and efficient towards selective light induced transformations.

As noted above, the hydrazide-based compounds can be prepared as a molecular scaffold to enable the scaffold to serve as a template for the formation of a desired compound or tagging of a compound with a functional group from the hydrazide-based scaffold. This can be achieved by substitution of the functional groups from the hydrazide-based compound attached as a substituent ($R_1$, $R_2$, $R_3$, $R_4$) to one of the nitrogen atoms by breaking of the N—N covalent bond. In certain embodiments, this can be done through click and unclick modes, thereby providing a versatile platform to tag different functionalities to other molecules.

Applicants have developed a strategy utilizing the excited state characteristics of hydrazide derivatives to undergo visible light mediated transformations (FIG. 1). According to methods of the invention, one of $R_1$, $R_2$, $R_3$, or $R_4$ of the hydrazide-based molecule is a photoreactive group. The molecular scaffold is subjected to visible light (i.e., irradiated with visible light) in the presence of a chemical reagent. A light mediated transformation occurs, i.e., the visible light causes excitation of the N—N bond so that the N—N bond breaks to form at least two newly separated functional groups comprising a nitrogen atom. At least one of the newly separated functional groups reacts with the chemical reagent to form a new molecule. Thus, the chemical reagent can be tagged or a desired molecule can be built. Any chemical reagent can be used that can bond with the separated functional groups. Preferred chemical reagents include bio-based reagents such as proteins and amino acids. In a preferred embodiment, the protein or amino acid contains a sulfur.

Traditional photoreactions that work under UV light have been carried out with visible light irradiation by incorporating hydrazide functional group. A diverse range of compounds are shown to react smoothly to afford products in high yields under environmentally benign conditions. Detailed photophysical experiments corroborate the experimental findings and highlight the role of excited state reactivity of these novel N—N bond based compounds.

The use of hydrazide derivative compounds has enabled Applicants to explore many of the classic reactions in photochemistry under visible light irradiations viz. [2+2]-photocycloaddition, 6π photocyclization, Paternò-Büchi reaction and Norrish-Yang cyclization. Without wishing to be bound by theory, it was envisioned that the presence of electron withdrawing carbonyl functionality and the loan pair on the nitrogen impart unique excited state characteristics that can be utilized for photochemical transformations.

The visible light mediated transformations can be particularly useful for tagging bio-based compounds such as proteins and amino acids. This can facilitate more robust imaging and sensing platforms for studying, monitoring, diagnosing, and sensing bio-based activities. In a preferred embodiment of the invention, the hydrazide-based compound can include a thiol group or thiol-based derivative, which allows for the functionalization of molecules including sulfur groups. Preferred molecules including sulfur groups can be amino acids and proteins.

Biomass Derived Renewable Polymers

Molecular scaffolds are prepared based on a phenacyl-derived compound isolated from biomass. A phenacyl group is an aromatic substituent that consists of a phenyl group attached to an acyl group. A molecule containing a phenacyl group has the formula RCH2(CO)C6H5 and the structure below. The phenacyl framework is versatile and can be functionalized to provide a template for the formation of desired compounds. For example, R, for denotes the remainder of the molecule; for instance, if R is Br, then the compound could be called "phenacyl bromide". The general structure of a phenacyl is:

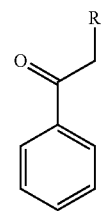

Where R, and/or any position on the benzene ring, can be a hydrogen, a halide, an organic functional group, or inorganic functional group. One of the R groups and/or any position on the benzene ring is a photoreactive group that is photoreactive to visible light. Non-limiting examples of suitable organic functional groups include, but are not limited to, an acid anhydride, an alcohol, an aldehyde, an alkane, an alkene, an alkyl, an alkyne, an amide, an amine, an arene, an azo compound, a cabamate, a carboxylic acid, an ether, an epoxide, an ester, an imine, an isocyanate, a ketone, a nitrile, a thiol, derivatives thereof, or combinations thereof. Non-limiting examples of suitable inorganic functional groups include, but are not limited to, those containing actinides, alkali metals, alkaline metals, metalloids, lanthanides, nitrogen-containing compounds such as nitrates and nitrites, phosphorus-containing compounds such as phosphates and phosphites, sulfur containing compounds such as sulfates, sulfites, and sulfonates, transition metals, derivatives thereof, and combinations thereof.

Illustrative first monomeric units include those that are specifically obtained from lignins. Lignin is a polymer and depolymerization thereof yields a variety of substituted phenols, of which p-coumaryl alcohol, coniferyl alcohol and sinapyl alcohol are the most abundant. Important, well-known phenolic derivatives of these compounds include vanillin, eugenol, iso-vanillin, iso-eugenol, caffeic acid and syringeugenol. In addition to the phenolic hydroxyl, these lignin derived monomers advantageously contain an additional functionality such as an aldehyde, an allyl or isoallyl. Other lignin-derived monomers that can serve as starting materials include creosol and guaiacol.

Illustrative starting materials for the synthesis of disclosed monomers can include not only phenols but also guaiacols, syringols, eugenols, catechols, their oxidized products, including vanillin, vanillic acid, syringaldehyde, and their easily-derived hydrocarbons, including benzene, toluene, xylene, styrene, biphenyls and cyclohexane. See "Top Value Added Chemicals from Biomass, Volume II: Results of Screening for Potential Candidates from Biorefinery Lignin," October 2007, Pacific Northwest National Laboratory for processes suitable for obtaining phenolic starting materials from lignin, and for additional examples of starting materials.

Illustrative bifunctional lignin derived monomers that can be utilized as first monomeric units include, without limitation, diacids, e.g., dials or dialdehydes which can contain 0, 1 or 2 methoxy groups depending on the starting material used. Examples of first monomeric units that contain 0 or 1 methoxy groups and alcohol, acid, or aldehyde functionalities include, without limitation:

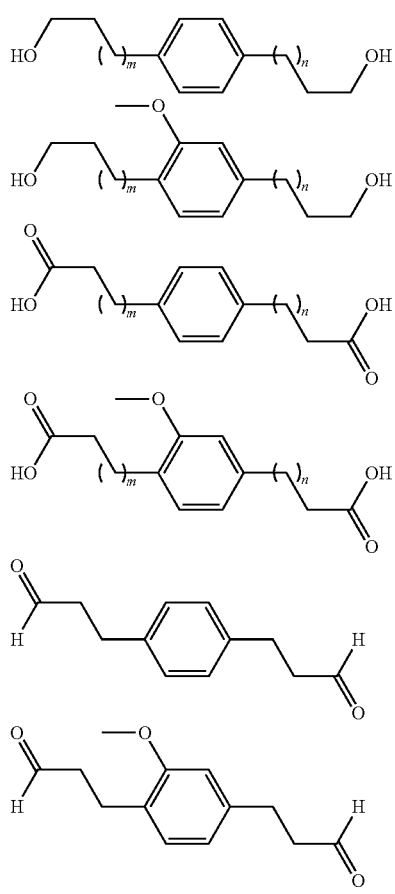

wherein m=0, 1, 2, 3, 4, 5, 6, 7, 8, 9, 10, 11, 12, 13, 14, 15, 16, 17, 18, 19, 20, or more, up to about 50; and n=0, 1, 2, 3, 4, 5, 6, 7, 8, 9, 10, 11, 12, 13, 14, 15, 16, 17, 18, 19, 20, or more, up to about 50; and where m=n or m≠n.

Dialdehyde monomers may be advantageously utilized herein as first monomeric units and illustrative chemistries for obtaining such monomers are described in the examples, below. Dialdehydes may be useful intermediates in that they can be readily converted to other functional groups, optionally including the addition of a hydrocarbon extension.

An example of a dialdehyde conversion to a diacid and then to a diol is as follows:

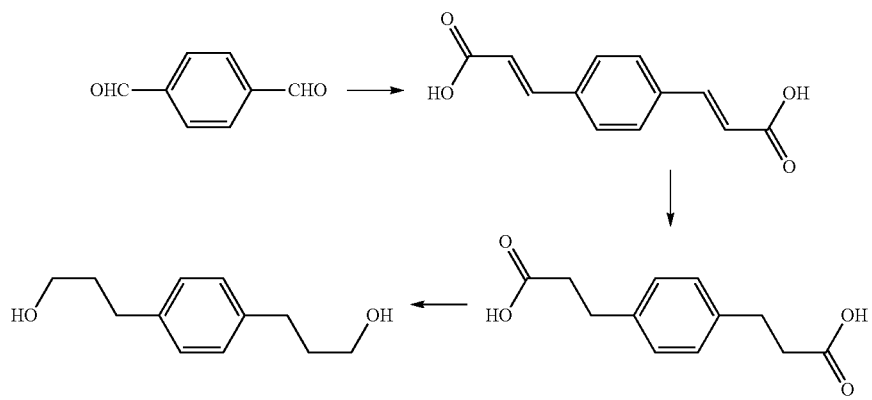

In general, aldehydes can be readily converted to another functional group of interest to form compounds, including for example disclosed compounds.

In some embodiments, compounds of formula I can be derived from lignins. In some embodiments, compounds of formula I can be derived from lignins that are depolymerized. In some such embodiments, depolymerized lignins include phenolic hydroxyl groups, which can be converted to leaving groups. In some embodiments, depolymerized lignins can be modified by extending the carbon chain, for example using Kumada coupling. In some embodiments, compounds of formula I can be derived from eugenol, isoeugenol, guiacol, vanillin, isovanillin, chavicol, chavibetol, or combinations thereof.

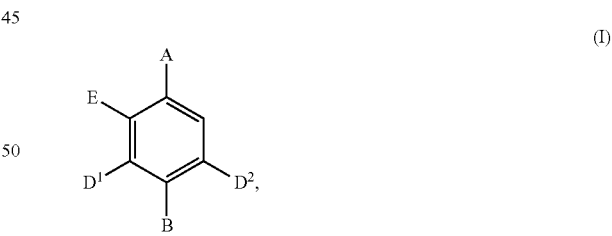

(I)

In some embodiments, compounds of formula I, as first monomeric units can be polymerized at least with second monomeric units. In some embodiments polymerization of compounds of formula I can be accomplished using free radical polymerization.

In some embodiments, the first monomeric units include those that are specifically obtained from itaconic acid. Itaconic acid, using the methods provided herein produce Methacrylic acids or derivatives thereof to produce the first monomeric units. The acrylic acid framework is versatile and can be functionalized to provide a template for the formation of desired compounds. Structure is provided below:

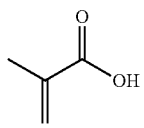

With respect to biomass derived from cellulose and hemicellulose, the present disclosure provides methods for the conversion of fructose, which is readily available from cellulose by degradation and isomerization, to a wide variety of monomers for polymer synthesis with novel properties. 5-Hydroxymethylfurfural (HMF) is a primary product of fructose dehydration and can serve as the starting material for the preparation of many of the furan-based compounds described herein. HMF can be converted to other important intermediates, such as 2,5-furandicarboxylic acid (FDCA), 2,5-diformylfuran, and 2,5-furylbis(propenoic acid), which can be utilized directly or can serve as further intermediates for the synthesis of additional monomers with the potential utility to replace terephthalic acid and other petroleum-derived monomers.

Examples of first monomeric units that can be derived from HMF can include those seen below:

rated into a polymer, is photocleavable. In some embodiments, the phototrigger can be cleavable using UV light, such as UV A or UVB light. In some embodiments, visible light can also be used to cleave the phototrigger. In some embodiments, cleavage can be accomplished in the absence of an additive (e.g., a sensitizer). In other embodiments, cleavage can be accomplished in the presence of an additive (e.g., a sensitizer).

Illustrative second monomeric units and the wavelengths that can be used to photocleave them are shown below and include, but are not limited to, nitrobenzyl, coumaryl, arylmethyl, benzoin, and phenacyl containing monomers. It should be understood that the illustrative substitution patterns are representative examples, and the compounds can be differentially substituted in order to carry out degradation.

Illustrative second monomeric units and the wavelengths that can be used to photocleave them are shown below and include, but are not limited to, nitrobenzyl, coumaryl, arylmethyl, benzoin, and phenacyl containing monomers. It should be understood that the illustrative substitution patterns are representative examples, and the compounds can be differentially substituted in order to carry out degradation.

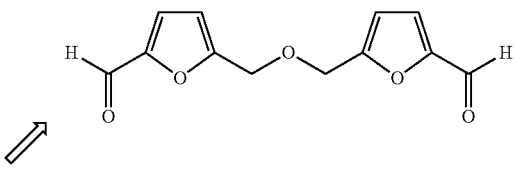

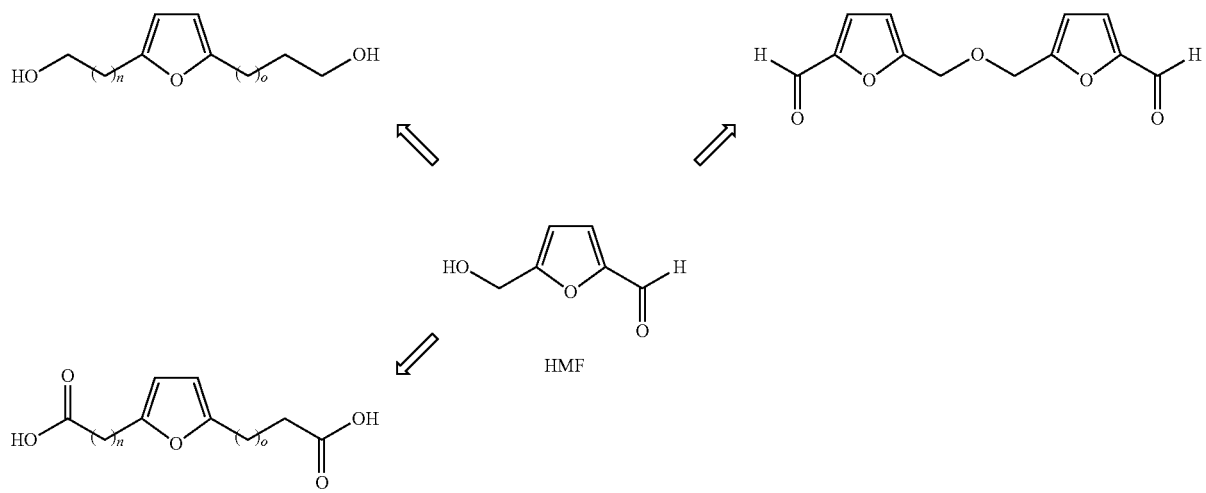

where n and o are independently selected from 0, 1, 2, 3, 4, 5, 6, 7, 8, 9, 10, up to 20, up to 30, up to 40 up to 50, or even higher.

Additionally, HMF and its 2,5-substituted derivatives can be reacted in a Diels-Alder reaction, followed by a deoxygenation/aromatization step to yield bicyclic naphthalene derivatives. A wide variety of symmetric and asymmetric naphthalene derivatives can be generated, since variation is introduced via the particular HMF derivative selected as a starting material.

Second Monomers

Disclosed photodegradable polymers also include at least one second monomeric unit which includes a phototrigger. A phototrigger may broadly contain one or more functionalities that, when incorporated into a polymer chain, impart photocleavability or photodegradability to the polymer. A phototrigger unit is cleavable with the addition of light of a wavelength that is specific to the particular type of phototrigger. The second, phototrigger containing, monomeric unit can be any bifunctional monomer that, when incorpo-

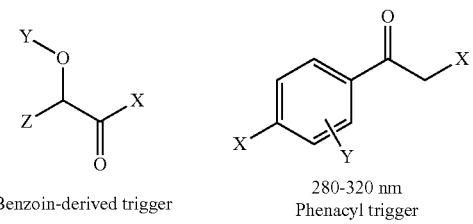

Benzoin-derived trigger 280-320 nm
Phenacyl trigger

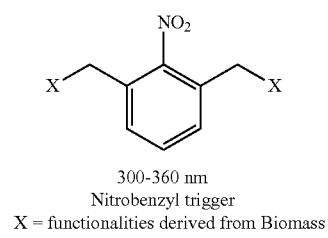

300-360 nm
Nitrobenzyl trigger

X = functionalities derived from Biomass

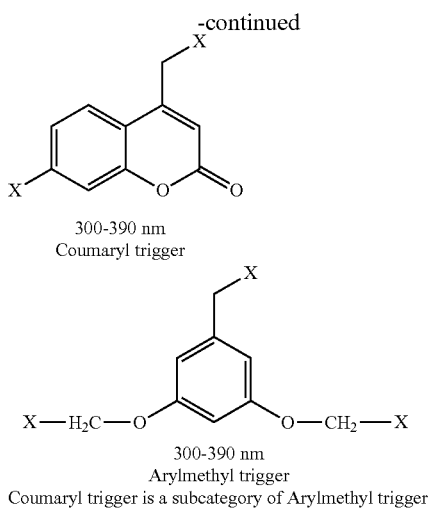

300-390 nm
Coumaryl trigger 300-390 nm
Arylmethyl trigger
Coumaryl trigger is a subcategory of Arylmethyl trigger In the above structures, it should be understood that "X" generally represents a functionality derived from biomass, e.g. one of the first monomers, and is not limited to any particular functionality or structure. "X" can also represent a functionality present on a third (non-biomass) monomeric unit, if a third unit is present in the polymer, and is also not limited to any particular functionality or structure. More broadly, any of "X", "Y" and/or "Z" can represent a linkage to a functionality present on a compound obtained from biomass (i.e., first monomeric unit as described herein) or present on an optional third monomeric unit in the photodegradable polymer.

In the photodegradable polymers of the invention, the phototrigger second monomeric unit can be linked to a first, biomass-derived monomeric unit at one, two or three positions as exemplified by linkages X, Y and/or Z in the above structures; the phototrigger second monomeric unit can optionally be linked to a third (non-biomass derived) monomeric unit (if present) at one, two or three positions as exemplified in the above structures; or any combination thereof. The linkages represented by "X", "Y" and/or "Z", can be the same, or they can be different.

The second, phototrigger monomer can, for example, contain any of hydroxyl, aldehyde, carboxylic acid, and the like at the "X" position prior to polymerization with a first biomass monomer or a third monomer that includes a compatible functionality so as to permit polymerization using standard polymerization chemistries. "X", "Y" and/or "Z" can include, for example and without limitation, alkyl, alkoxy, or aryl. "Y" can include, for example, a functionalized group such as OCHz-X where X represents a linkage to a biomass-derived component.

Optionally, the photodegradable polymer further includes at least one third monomeric unit, wherein the third monomeric unit is obtained from a petroleum product or is chemically or enzymatically synthesized. The optional third monomeric unit can be, for example, a hydrophilic monomer, such as an alkylene glycol.

The third monomeric unit, when present, can be selected to increase solubility of the polymer, to impart additional functionality to the resultant polymer, or to provide any desired properties. The optional third monomeric unit can impart additional functionality for example, by providing a site for cross-linking or further derivatization. An illustrative third monomeric unit is an alkylene glycol, such as ethylene glycol or propylene glycol; other examples of third monomeric units include, without limitation, cationic salts, anionic salts such as carboxylates or sulfonates, 1,4-butanediol, 1,6-hexanediol, 2,5-cisbis(hydroxymethyl)tetrahydrofuran, and 1,6-hexamethylenediamine. The polymer may include a single third monomeric unit, or a plurality of different third monomeric units. In some embodiments, the third monomer includes an amine to increase solubility of the polymer and/or provide additional functionality.

The first, second and optional third monomeric units are at least bifunctional in order to facilitate polymerization; in some embodiments, the constituent monomers are compatibly bifunctionalized, such that a functional group of one bifunctionalized monomer is able to react with a chemically compatible functional group of another bifunctionalized monomer to form a covalent linkage. For example, the first, second or optional third monomeric unit can be a diol, a diacid, a diester, a dialdehyde, a diamine, a diallyl, a diether, a carbamate, an anhydride, a diamide, a diisocyanate, a diepoxide and/or a diaziridine. Illustrative functionalizations can include hydroxyl, aldehyde, carboxylic acid, amine, amide, ester, vinyl, or allyl group. In some embodiments, the functional groups on an individual monomeric unit are the same (e.g., two hydroxyl groups, or two acid groups) but they may be different. Polyfunctionalized monomers can be symmetric or asymmetric. Monomeric units incorporating one or more aldehyde, carboxylic acid, amine, or alcohol may be especially useful as they can generally be interconverted, as well as extended by the addition of carbon fragments, using standard chemistries. The first, second and optional third monomeric units may be selected to permit polymerization; for example, the first, biomass-derived monomeric unit can be a diol, and the second monomeric unit constituting the phototrigger can be a diacid. In some embodiments, when an optional third monomeric unit is incorporated into the polymer, it can have the same functionality as the second, phototrigger monomeric unit. For example, if the second, phototrigger monomeric unit is a diol, the third monomeric unit can also be a diol, such that both are capable of reacting with a diacid first monomeric unit derived from biomass.

Disclosed polymers may contain any amounts of first, second and optional third monomers. In some embodiments of the polymer, the polymer may contain a higher number of first and/or third monomeric units than second (phototrigger) monomeric units. The ratio of first:second:third monomeric units (x:y:z) can be any selected ratio, reflecting for example the desired properties of the polymer and/or its intended use. An example of the ratio x:y:z is 1:0.1:0.9 where x is 1, y in 0.1 and z is 0.9.

The polymers of the invention, derived from renewable resources, may be characterized by higher degrees of degradability and sustainability. The built-in photocleavable unit(s) result in photodegradable polymers that can be pre-programmed for degradation with light of a chosen wavelength, for example UV irradiation.

In some embodiments, photolytic decomposition of the polymer can optionally be followed by isolation, purification and/or recovery of one or more constituent monomeric or oligomeric units. In some embodiments, a monomeric or oligomeric unit derived from biomass can be isolated, purified, and/or recovered from decomposed polymer, which can in turn be reused or recycled, for example as components of other polymers, thereby minimizing the impact on the environment and making the process both green and sustainable. The examples below show that monomers produced after photodegradation can be successfully reused to build the polymer.

The invention thus includes methods of polymerizing the first, second and optional third monomers to form a polymer, as well as uses of the polymer in commercial, industrial, and medical applications, for example as coatings, adhesives, oils, gels, films, paints, and the like. Polymers of the invention may include nylons, polyesters, polyurethanes, polyamides and the like. The invention further includes a method for degrading the polymer of the invention by exposing the polymer to radiation, for example UV irradiation at a selected wavelength, and for a time sufficient, to photocleave the polymer. For example, the solid polymer can be ground, a solvent added (e.g., THF/water) and the mixture can be irradiated with UV light for a time sufficient to achieve photocleavage. Degradation can alternatively take place in the powder form. Optionally, the degradation products, particularly the product derived from biomass, can be isolated, purified and/or recovered and reused.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

EXAMPLES

Embodiments of the present invention are further defined in the following non-limiting Examples. It should be understood that these Examples, while indicating certain embodiments of the invention, are given by way of illustration only. From the above discussion and these Examples, one skilled in the art can ascertain the essential characteristics of this invention, and without departing from the spirit and scope thereof, can make various changes and modifications of the embodiments of the invention to adapt it to various usages and conditions. Thus, various modifications of the embodiments of the invention, in addition to those shown and described herein, will be apparent to those skilled in the art from the foregoing description. Such modifications are also intended to fall within the scope of the appended claims.

Example 1

Enabling Traditional Photoreactions to Work Under Visible Light.

Figure 2:
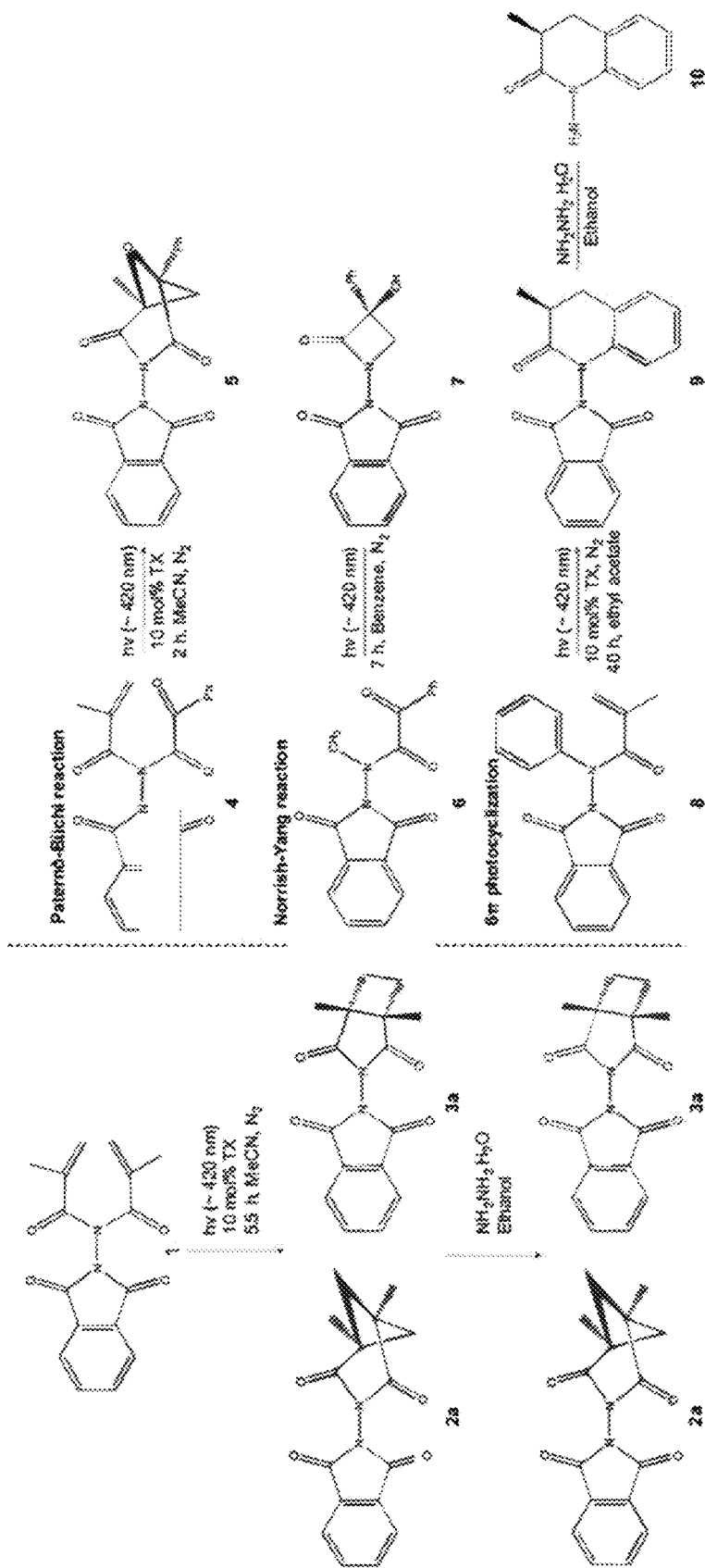
FIG. 2 shows a scheme of phthalimide based hydrazide derivatives as model systems for initiating traditional photoreactions with visible light.
Figure 3:
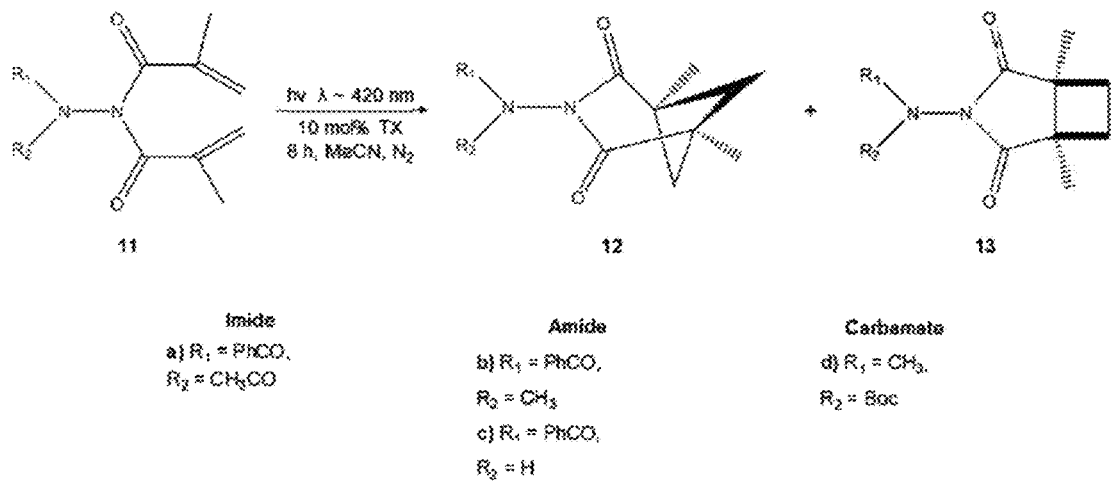
FIG. 3 shows a scheme evaluating hydrazide based on non-cyclic Imide, amide and carbamates for excited state transformations promoted by visible light.

To test the theory that the presence of electron withdrawing carbonyl functionality and the loan pair on the nitrogen impart unique excited state characteristics that can be utilized for photochemical transformations, substrates were built that featured N—N bonds (FIGS. 2 and 3). They were evaluated for various photoreactions. The substrates were synthesized from the corresponding N-amino derivatives in good yields and were subjected to photochemical reactions (Tables 1-5). The substrates and photoproducts were characterized by 1H and 13C NMR spectroscopy and HRMS. In some cases to avoid ambiguity in structure elucidation, the characterization was performed using single crystal X-ray analysis.

To elucidate the light induced transformation of N—N derivatives (FIG. 2) for different transformations we evaluated their reactivity under direct irradiation conditions as well as under sensitized irradiation with visible light with thioxanthone acting as a photosensitizer. To establish the reaction conditions, we first evaluated phthalimide-based hydrazides 1, 3, 5 and 7 for [2+2]-photocycloaddition, Paternò-Büchi reaction, 6π photocyclization and Norrish-Yang reaction respectively leading to the corresponding photoproducts (FIG. 2). Inspection of Table 1 shows that upon employing 1-10 mol % of thioxanthone sensitizer in acetonitrile led to effective transformation of phthalimide substrates to the corresponding photoproducts. [2+2]-Photocycloaddition of 1 in the presence of 1, 5 and 10 mol % of thioxanthone (~420 nm irradiation) led to cyclobutane product in 8, 39 and 100 conversion respectively (Table 1; entries 2-4). The ratio of 2a and 3a (cross:straight photocycloaddition) was 83:17 with an isolated yield of 71% (with 10 mol % of thioxanthone as the sensitizer). The phthalimide unit was removed by treatment with hydrazine hydrate to yield the corresponding N-amino derivative 3a and 3b.

Irradiation of 1 with ~420 nm in the absence of thioxanthone did not result in any noticeable conversion with complete recovery of the reactant. This showed that a traditional [2+2] photoreaction that occurred with UV light could be fine-tuned to occur under visible light sensitization.

TABLE 1

Conversion studies with different loading level of the thioxanthone (TX) for visible-light mediated photoreactions.[a]

| Entry | Tx (mol %) | % Conversions (% isolated yield)[b] | | |
|---|---|---|---|---|
| | | 1 | 4 | 8 |
| 1 | 0 | 0 | 19 | 7 |
| 2 | 1 | 8 | 26 | 88 |
| 3 | 5 | 39 | 100 | — |
| 4 | 10 | 100 (71) | 100 (88) | 90 (62) |

[a] Unless otherwise noted all irradiations were performed at room temperature in HPLC grade acetonitrile with no optical density at irradiation wavelength; TX = thioxanthone; [1] = 3.35 mM, hv time = 5.5 h; [4] = 3.33 mM, hv time = 2 h; [8] = 3.26 mM; hv time = 40 h. Reported values are an average of a minimum of 3 trials (±5% error).
[b] % Conversion calculated by $^1$H NMR spectroscopy using triphenylmethane as internal standard. Isolated yields in parenthesis.

TABLE 2

Solvent screening for visible-light photoreactions.[a]

| | | % conversion | | | |
|---|---|---|---|---|---|
| Entry | Solvent | 1 | 4 | 6[b] | 8 |
| 1 | Methanol | 100 | —[c] | —[c] | 91 |
| 2 | Acetonitrile | 100 | 100 | 16 | 90 |
| 3 | Ethyl acetate | <7 | 78 | 55 | 100 |
| 4 | Benzene | 63 | 100 | 80 | 60 |
| 5 | Methylcyclohexane | 0 | 71 | —[d] | 71 |

[a] Irradiations were performed at room temperature with HPLC grade solvents with no optical density at irradiation wavelength with 10 mol % of thioxanthone as sensitizer. Rayonet reactor equipped with ~420 nm tubes (16 tubes × 14 W each) was employed. [1] = 3.35 mM, hv time = 5.5 h; [4] = 3.33 mM, hv time = 2 h; [6] = 5.1 mM, hv time = 7 h and [8] = 3.26 mM, hv time = 40 h. Reported values are an average of a minimum of 3 trials (±5% error). % conversion calculated by $^1$H-NMR spectroscopy using triphenylmethane as internal standard.
[b] Direct irradiation of 6 without thioxanthone.
[c] decomposition observed.
[d] No reaction observed.

Building on this result, we evaluated Paternò-Büchi reaction of 4 in the presence of 1, 5 and 10 mol % of thioxanthone (~420 nm irradiation) leading to the corresponding oxetane photoproduct 26, 100 and 100 conversion respectively (Table 1; entries 4-6) with an isolated with 88% yield (with 10 mol % of thioxanthone as the sensitizer). Irradiation of 4 with ~420 nm in the absence of thioxanthone led to 5 with 19% conversion. Similarly, 6π photocyclization of 8 in the presence of 1 and 10 mol % of thioxanthone (~420 nm irradiation) led to the corresponding 3,4-dihydroquinolin-2-one photoproduct 9 in 88 and 90 conversion respectively (Table 1; entries 4-6) with an isolated with 62% yield (with 10 mol % of thioxanthone as the sensitizer). Direct irradiation of 8 at ~420 nm (Rayonett irradiation) resulted in 9 with 7% conversion. In the case of Norrish-Yang reaction, due to absorptivity of 6 in the visible region, direct irradiation was evaluated in MeCN that led to β-lactam photoproduct 7 in 16% con-version (Table 2). In order to improve the yield of β-lactam photoproduct 7 during Norrish-Yang reaction of 6, we evaluated the reaction in solvents (Table 2). The reaction conversion was 80% and 55% in benzene and ethyl acetate (Table 2; entries 3 and 4). Similarly, the reaction of 1 in methanol (Table 2; entry 1) gave quantitative con-version (similar to acetonitrile) of the cycloaddition product (2:3=83:17). Benzene and acetonitrile was found to be the best solvent of choice for Paternò-Büchi reaction of 4 leading to oxetane product 5 (Table 2; entry 4). 6π-Photocyclization of 8 was efficient in all the solvents investigated with moderate conversion in benzene and methylcyclohexane (MCH) and 90 to quantitative conversions in methanol, acetonitrile and ethyl acetate.

Figure 4:
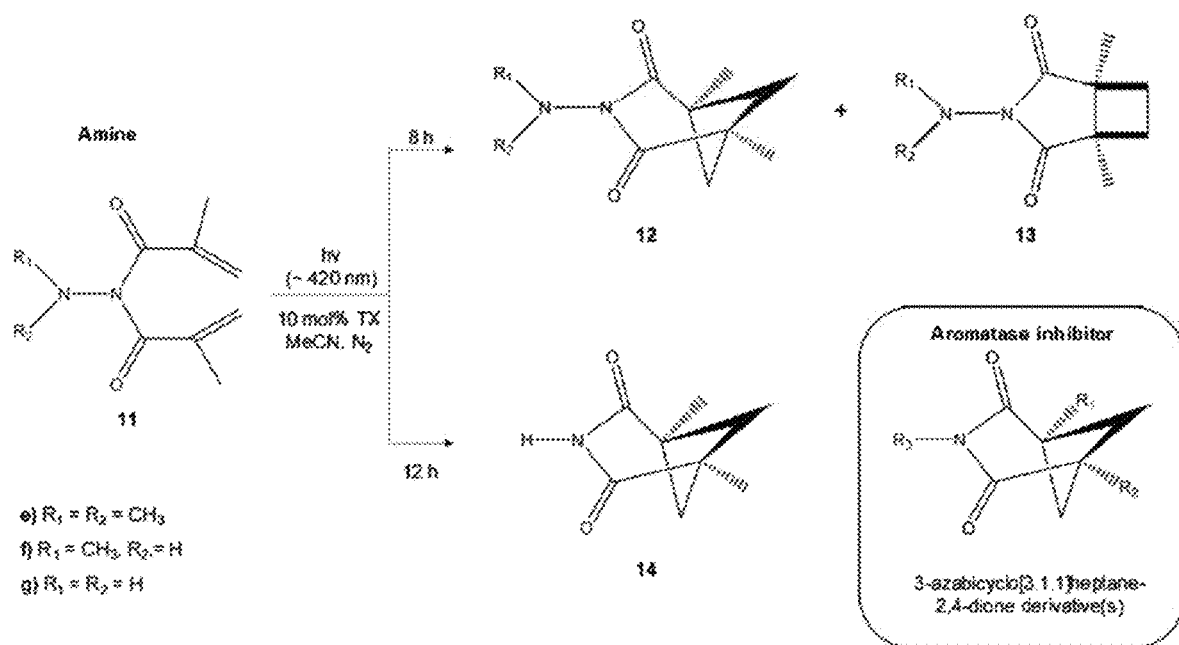
FIG. 4 shows a scheme evaluating hydrazide based on non-cyclic amines for excited state transformations promoted by visible light.

Having established the usefulness of phthalimide based systems (FIG. 2) to promote traditional photochemical reactions under visible light irradiations; the features necessary for generalizing the chromophore responsible for photochemical reactivity under visible light irradiation were evaluated. To accomplish this, we synthesized N—N based photoactive chromophores 11a-g (FIGS. 3 and 4) to evaluate the role of phthalimide functionality in the photochemical reaction. Based on the reactivity of 1 that underwent photocycloaddition, we designed N—N based system with di-methacryloyl functionality on one nitrogen and one of the following functionalities in the $2^{nd}$ nitrogen viz., imide 11a; 3° amide 11b; 2° amide 11c; carbamate 11d; 3° amine 11e; 2° amine 11f and 1° amine 11g.

Inspection of Table 3 reveals that the photoreaction 11 in acetonitrile under visible light irradiation in the presence of 10 mol % thioxanthone was dependent on the hydrazide functionality. Photoreaction of 11a that features a imide functionality resulted in 56% conversion with 52% isolated yield (Table 3; entry 1). Changing the functionality from an imide to an amide resulted in either decomposition (with 3° amide 11b; Table 3; entry 2) or no observable product formation (with 2° amide 11b; Table 3; entry 3). Changing the functionality from to a carbamate 11d resulted 82% conversion with 29% yield (Table 3; entry 4). We then changed the functionality to N-substituted amines 11e-g. Tertiary and secondary amine derivatives 11e and 11f gave 95% (40% yield; 12e:13e=70:30) and 97% (40% yield; 12f:13f=80:20) respectively (Table 3; entries 5 and 6). There was no observable reaction with 1° amine derivatives 11g (Table 3; entry 7). To further probe the reactivity of amines, we selected 11e to investigate the effect of solvents and loading level of thioxanthone sensitizer. Changing the mol % of thioxanthone from 1, 5 to 10 resulted in 74%, 93% and 95% conversions respectively. The reaction with 10 mol % of thioxanthone was also effective in ethyl acetate and benzene with 55% and 52% conversions respectively.

TABLE 3

Photocycloaddition of 11 by visible-light using 10 mol % of thioxanthone (TX) in acetonitrile. [a]

| Entry | Substrate [b] | % Convn. [c] | % Yield [c] | 12:13 [c] |
|---|---|---|---|---|
| 1 | 11a | 56 | 52 | —[d] |
| 2 | 11b | —[e] | — | — |
| 3 | 11c | —[f] | — | — |
| 4 | 11d | 82 | 29 | —[d] |
| 5 | 11e | 95 | 40 | 70:30 |
| 6 | 11f | >99 | 40 | 80:20 |
| 7 | 11g | —[f] | — | — |

[a] Irradiations (8 h) were performed at room temperature unless otherwise noted using a Rayonet reactor equipped ~420 nm (16 bulbs × 14 W each). Reported values are an average of a minimum of 3 trials (±5% error).
[b] [11a] = 3.18 mM; [11b] = 3.49 mM; [11c] = 3.67 mM; [11d] = 3.54 mM; [11e] = 5.1 mM; [11f] = 5.49 mM; and [11g] = 2.38 mM.
[c] % conversion, yields and 12:13 ratio calculated by $^1$H-NMR spectroscopy using triphenylmethane as internal standard.
[d] ratios not determined due to overlapping peaks in 1H NMR spectroscoepy.
[e] decomposition observed.
[f] no reaction observed.

To appreciate the role of hydrazide functionality in promoting established photochemical reaction with visible light, it became necessary to understand the mechanistic details to rationalize the reactivity. Based on our experimental conditions and observations, the photoreactivity of hydrazides with thioxanthone sensitization can occur either by energy transfer or electron transfer. To ascertain the feasibility of electron transfer, we ascertained the oxidation and reduction potentials of thioxanthone and hydrazine derivatives 1, 4, 6, 8 and 11 by cyclic voltammetry measurements. The free energy for electron transfer from excited thioxanthone to N—N based substrates were calculated using Rehm-Weller equation. In all the cases, the free energy was negative ranging from −1.6 kcal/mol to −15.4 kcal/mol indicating that an electron transfer is feasible in which thioxanthone acts as the donor (to radical anion) and the hydrazide derivatives act as an acceptor (forming radical anion).

To evaluate the feasibility of energy transfer initiating the reaction detailed photophysical studies were carried out. Based on the investigation with hydrazide systems, light induced transformations can have divergent pathways viz., energy transfer and electron transfer pathways depending on the nature of substrate(s) and reaction conditions.

References:
(1) Jin, J.; MacMillan, D. W. C. Alcohols as alkylating agents in heteroarene C—H functionalization. *Nature* 2015, 525, 87-90.
(2) Prasad Hari, D.; Hering, T.; König, B. The Photoredox-Catalyzed Meerwein Addition Reaction: Intermolecular Amino-Arylation of Alkenes. *Angewandte Chemie International Edition* 2014, 53, 725-728.

Example 2

Photochiral Auxiliaries based on restricted N—N bond Rotations: Visible Light Mediated 6π-Photocyclization Atropisomers based on C—N bond rotations have been extensively studied as they are extensively utilized for methodology development in thermal and photochemical reactions. Due to its significance, uncovering compounds that will not only feature atropisomerism but also feature unique photochemical and photophysical properties would provide a significant advancement. In that regard, we became interested in developing model systems that will feature a N—N chiral axis as we envisioned such system be amenable to the removal of atropisomeric after chemical transformations, cleaving and thus removing the axial chirality in the resultant.

Based on literature precedence related to the stereodynamics[1] diacylation of N—N bond (one acyl group on each nitrogen) in restricted bond rotation ($\Delta G^{\ddagger}_{rac}$~23 kcal/mol, $T_c$=188° C.).[2] This restriction bond around N—N bond arises from a combination of electronic effects and molecular asymmetry.[3] The unusual rotational barrier for a heteroatom-heteroatom bond relates to the repulsion of lone pairs when in the vicinity in addition to the geometrical conformational preferences required by the heteroatom.[4] For the tetraacylated acyclic hydrazides the barrier to the rotation was found to be even more considerable ($\Delta G^{\ddagger}_{rac}$~23 kcal/mol, $T_c$=420° C.).[1c-e, 5]

Figure 5:
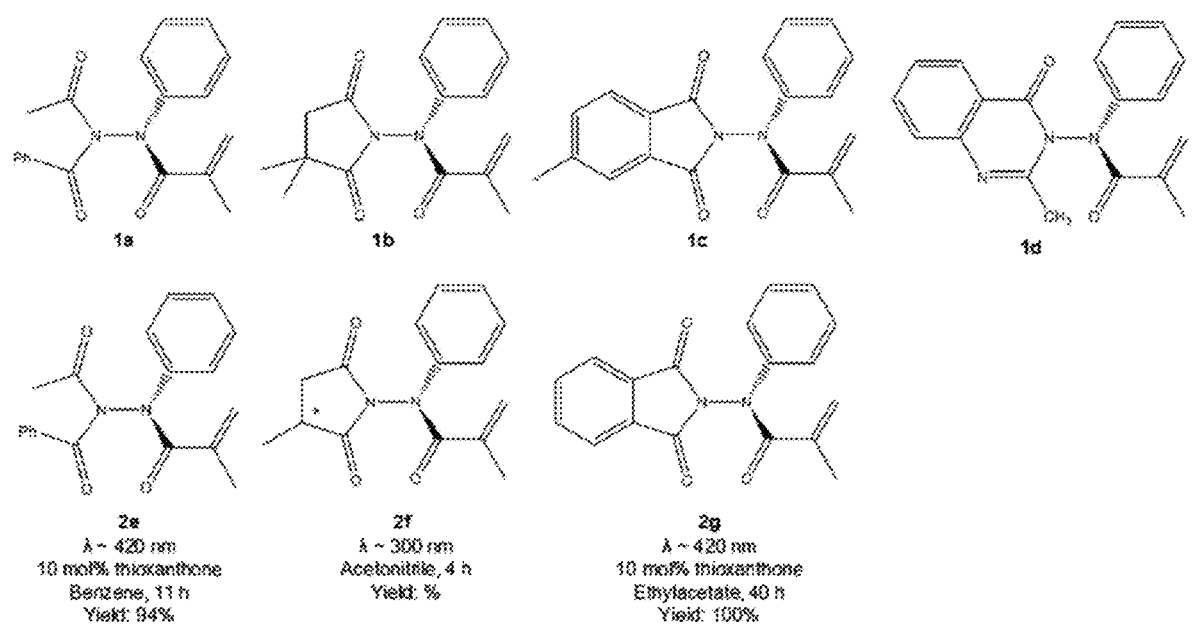
FIG. 5 shows stable and isolable N—N bond based atropisomers for atropselective photoreactions.
Figure 6:
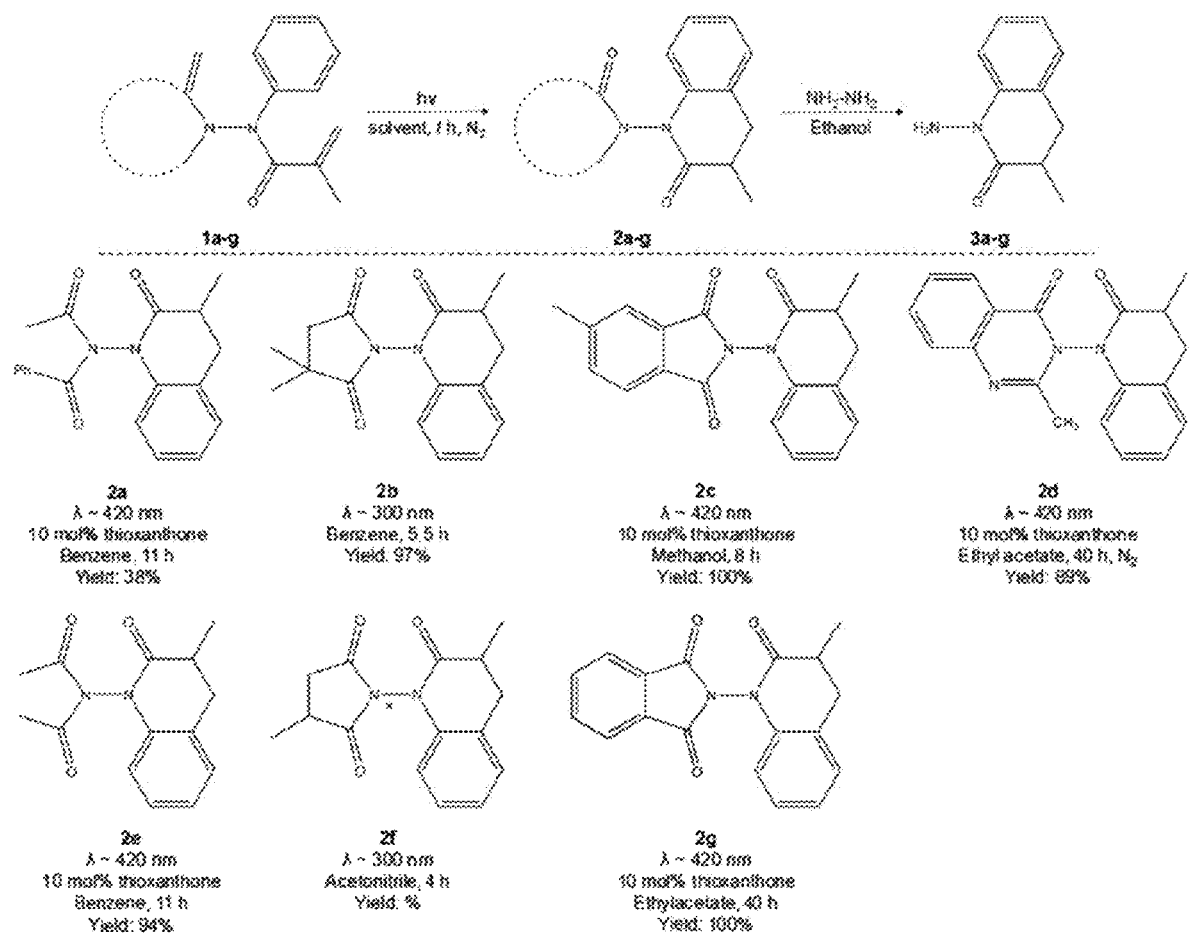
FIG. 6 shows 6π-Photocyclization of hydrazides by UV and visible light.

In order to expand upon this precedent, we synthesized acyclic hydrazides 1a-d (FIG. 5). The design of these hydrazides featured two main components viz., a) one of the hydrazide nitrogen was dissymmetrically substituted either with a imide (acyclic imide as in 1a or cyclic imide as in 1b-c) or quinazolinone functionality (as in 1d) and b) viz., a) the second hydrazide nitrogen features both a phenyl and methacryloyl substituents that was tailored for evaluating 6π-photocyclization. The reason we envisioned such was due to the anticipated photochemical and photophysical properties as well as easy cleavage of N—N bond that will provide easy access to N-amino-3.4-dihydro-3,4-quinolin-2-one 3 from the cyclized photoproduct 2 (quae vedere; FIG. 6).

The synthesis of N—N bond based compounds where N—N bond does not constitute to be a part of the ring system is not well documented in the literature. One elegant methodology developed by Baran and coworkers utilizes electrochemical technique for accessing N—N bond based dimeric indole alkaloids.[6] However, its limitation stems from the requirement of dimeric species to be the product. Hence, we developed synthetic routes to access atropisomeric hydrazides.

Figure 7:
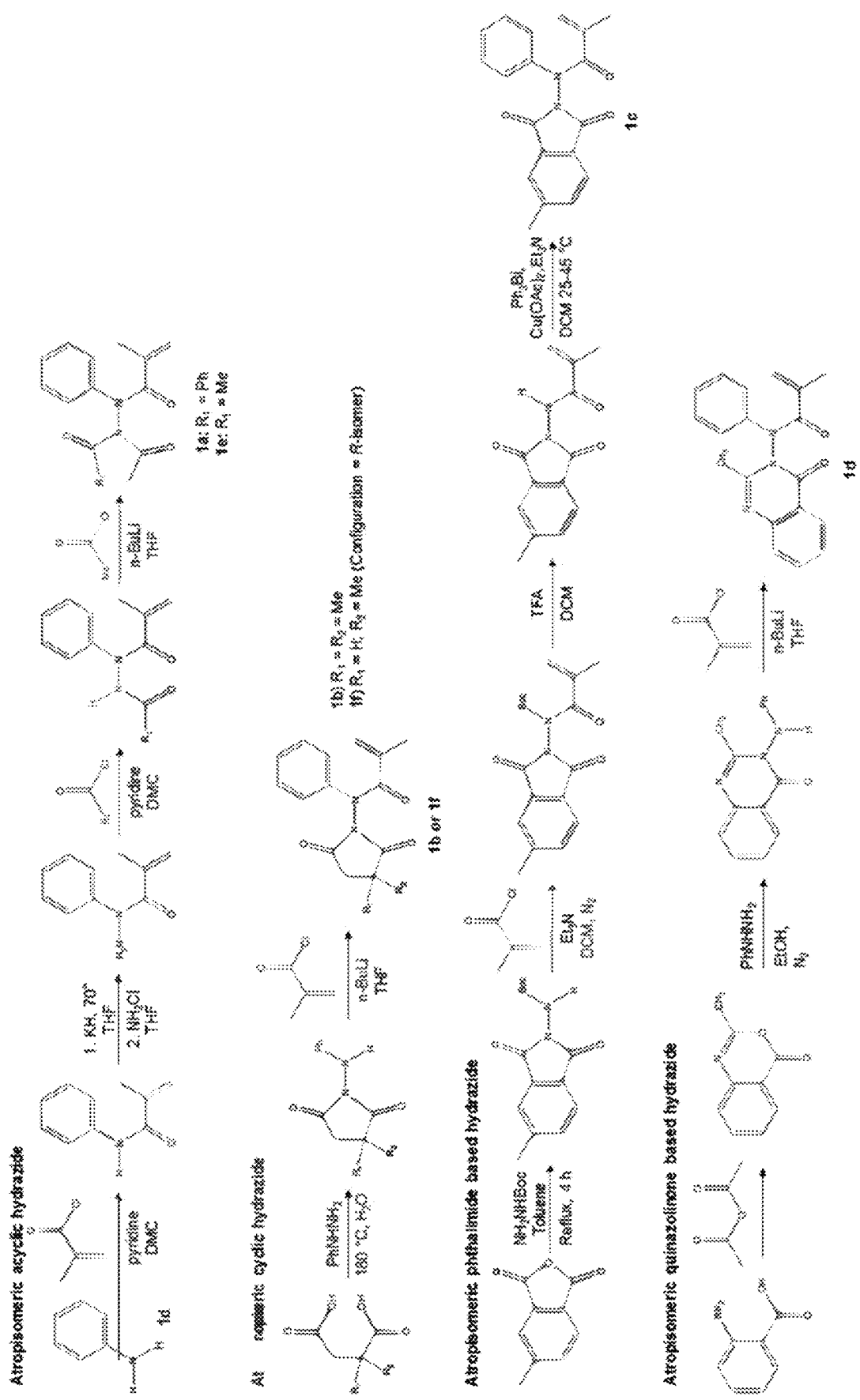
FIG. 7 shows the synthesis of atropisomeric hydrazides.

For the synthesis of acyclic hydrazides 1a and 1e, the approach was straightforward that involved the synthesis of N-amino acrylanilides (FIG. 7) that was subsequently acylated with appropriate acylating agent to yield 1a or 1b. to give and then constructed the full skeleton. A point to note is that N-amination is an useful handle in hydrazide synthesis for a two-nitrogen synthon.[7] We resorted to monochloramine as the source for $NH_2^+$ owing to the ease in reagent preparation, toxicity and stability issues that relates to the synthesis of traditional electrophilic aminating agents.[8] A point to note is that the N-aminated acrylanilides were found to be unstable for storage and required to be consumed immediately for the next step in the synthesis. The acylated hydrazides showed to be highly stable at room temperature. For synthesizing atropisomeric succinimide based hydrazide 1b (FIG. 7) we utilized phenyl hydrazine as the two-nitrogen synthon. Despite of existing literature precedence for the synthesis of N-Phenylaminopyrrolidine-2,5-dione derivative[9], we wanted to ascertain that the other likely product of reaction i.e. tetrahydrophenylpyridazinedione[10] derivative was not formed while heating a cyclic imide with phenyl hydrazine under dehydrating conditions. In addition, Conley and coworkers have reported several single crystal XRD structures showcasing ambiguity in literature in regards to the existing synthetic routes for N—N bond based imides. 11 The synthesis of desired imide based anilide was confirmed by single crystal XRD structure. The next step in synthesis was acylation with methacryloyl chloride. The acylation was not as simple as expected and required the deprotonation of the N—H hydrogen by a strong base. The desired acrylanilide 1e was successfully synthesized in a two high yielding steps and was confirmed by 1H NMR spectroscopy, HRMS and XRD. For the synthesis of atropisomeric phthalimide based hydrazide 1c (FIG. 7) we utilized 2-tert-butyl carbazate as a two-nitrogen synthon in an approach similar to Abbas[12] and Brosse[13] and co-workers for the synthesis tert-Butyl (1,3-dioxoisoindolin-2-yl) carbazate derivatives. The reaction gave us quantitative yields of desired N-(tert-Butoxycarbonylamino) phthalimide derivative. The final N-arylation of was performed using copper and triarylbismuth in the presence of tertiary amine as a promoter. 14 For quinazolinone based atropisomeric hydrazide 1d, we started with anthranilic acid, which on ring cyclization afforded us the benzoxazine derivative. For the subsequent steps the synthetic protocol was similar to the synthesis of 1b utilizing phenyl hydrazine resulting in atropisomeric hydrazide 1d in three simple and very high yielding steps (FIG. 7).

To ascertain the rotation barrier around N—N bond racemization kinetic measurements were performed with atropisomeric hydrazides 1. We first evaluated asymmetrically substituted acyclic hydrazide 1a, acyclic hydrazide 1b and phthalimide based hydrazide 1c. that happens to be a triacylated hydrazide. To our disappointment, we could not observe separation of the individual atropisomers of 1a and 1c by HPLC analysis with the chiral stationary phase that was available under our disposal. In case of succinimide hydrazide 1b, we observed a fast rotation around the N—N bond a that was reflected in the separation profile on the HPLC chromatogram.[15] The peak shape characteristics reflected two resolved peaks that do not reach the baseline (plateau).[16] This gave us some lead in developing atropisomeric hydrazide 1d that featured quinazolinone functionality.[17 1b, 18] The individual P and M atropisomers of 1d were separated by the HPLC on a chiral stationary phase that enabled us to determine the racemization rate constant ($k_{rac}$), the half-life of racemization ($t_{1/2-rac}$), and the activation energy of racemization ($\Delta G^{\ddagger}_{rac}$). As the optically pure atropisomeric 1d were stable at room temperature, racemization kinetic measurements were performed at 45° C. The barrier for racemization ($\Delta G^{\ddagger}_{rac}$; at 45° C.) in ethyl acetate and benzene was found to be ~24.2 kcal/mol and 23.9 kcal/mol respectively. Hence the half-life was computed to 1.29 days in ethylacetate and 0.89 days in benzene.

TABLE 4

Racemization parameters for optically pure atropisomers of 1d at 45° C. [a]

| Entry | Solvent | $k_{rac}$ (S$^{-1}$) | $\tau_{1/2}$ (days) | $\Delta G^{\ddagger}$ rac (kcal.mol$^{-1}$) |
|---|---|---|---|---|
| 1 | Ethyl acetate | 16.4 × 10$^{-5}$ | 1.20 | 24.2 |
| 2 | Benzene | 2.15 × 10$^{-5}$ | 0.89 | 23.9 |

[a] Values carry an error of ±5%. The kinetics of racemization was ascertained by HPLC equipped with a chiral stationary phase.

The 6π-photocyclization of N—N bond based acrylanilides 1a-g by UV/visible light irradiation was facile at room temperature (FIG. 6). Except for the succinimide based acrylanilide 1b all the other substrates underwent a facile visible light mediated photocyclization with thioxanthen-9-one (TX) acting as a sensitizer/photocatalyst. The photocyclization were clean which was reflected in excellent yields in dihydroquinolinone based photoproduct 2 (FIG. 6). For each substrate a systematic solvent screening (Table 5) was performed to arrive at the conditions that were suitable for achieving high yields of the photoproducts. In methylcyclohexane (MCH) 1a and 1c decomposed during sensitized irradiation with TX and in case of the quinazolinone based acrylanilide 1g there was no observable photoproduct. Based on the solvent studies ethyl acetate became the solvent of choice for investigating visible light mediated 6π-photocyclization for 1a-g.

TABLE 5

Solvent effects and sensitizer loading studies during 6π-Photocyclization of hydrazides by UV and visible light.

| Entry | Substrate [b] | λ (nm) [c] | t (h) | Solvent [d] | % Yield [e] |
|---|---|---|---|---|---|
| 1 | 1a | 420 | 40 | Ethyl acetate | 100 |
| 2 | 1b | 420 | 11 | Benzene | 94 |
| 3 | 1c | 420 | 11 | Benzene | 38 |
| 4 | 1d | 420 | 8 | Methanol | 100 |
| 5 | 1g | 420 | 40 | Ethyl acetate | 89 |

[a] Irradiations were performed at room temperature, Sens.: Sensitizer ( TX: thioxanthone);
[b] [2a] = 3.26 mM; [2b] = 3.84 mM; [2c] = 3.1 mM; [2d] = 3.12 mM; and [2g] = 3.13 mM.
[c] Rayonet reactor equipped with ~420 nm tubes (16 tubes, 14 W each) or with ~300 nm tubes (16 tubes, 12 Watt) was employed.
[d] Solvents used had no optical density at irradiation wavelength.
[e] % NMR Yields carry an error of ±5% and was calculated by $^1$H NMR spectroscopy using triphenylmethane as internal standard.

Having ascertained the best solvent we shifted our attention towards sensitizer loading levels. The acyclic hydrazide 1a showed the photocyclization was possible at as low as 1 mol % of the sensitizer loading. A similar observation was noted for phthalimide-based hydrazide 1c. In case of 1d photocyclization was efficient at 5 mol % loading of the TX sensitizer loading with ~80% conversion/

To highlight the versatility of our strategy large-scale visible light mediated photocycloaddition of 1d was performed under optimized conditions in Rayonet Reactor equipped with ~420 nm tube lights. The photoproduct 2d was isolated in XX % yield that was then n subjected to reflux with hydrazine hydrate for the removal of phthalimide ring. This provided us a convenient access to N-amino-3,4-dihydroquinoline-((1H)-2-one) 3 a potential monoamine oxidase inhibitor (FIG. 5).[19]

Applicants have shown hydrazides with appropriate substitutions feature a restricted N—N bond rotation that results in stable and separable atropisomers. In addition, the N—N bond severed as an excellent chromophore to promote atropselective photochemical reaction leading to high enantioselectivity in the photoproduct. Based on photophysical and photophysical studies during atropselective 6π-photocyclization of acrylanilides the unique nature of atropisomeric hydrazides serving as a "photochiralauxiliary" was uncovered.

References (1) (a) Ottersbach, P. A.; Schnakenburg, G.; Gutschow, M. Chemical communications 2012, 48, 5772-5774. (b) Arthur, R. J.; Coogan, M. P.; Casadesus, M.; Haigh, R.; Headspith, D. A.; Francesconi, M. G.; Laye, R. H. CrystEngComm 2009, 11, 610-619. (c) Kim, Y. J.; Lee, D. Organic Letters 2004, 6, 4351-4353. (d) Coogan, M. P.; Ooi, L.-1.; Pertusati, F. Organic & biomolecular chemistry 2005, 3, 1134-1139. (e) Al-Sehemi, A. G. Journal of King Abdulaziz University 2006, 18.

(2) (a) Bishop, G. J.; Price, B. J.; Sutherland, I. O. Chemical Communications (London) 1967, 672-674. (b) Moriarty Sr, R. M.; Murphy, M. R.; Druck, S. J.; May, L. Tetrahedron Letters 1967, 8, 1603-1609.

(3) (a) Coogan, M. P.; Passey, S. C. Journal of the Chemical Society, Perkin Transactions 2 2000, 2060-2066. (b) Verma, S. M.; Prasad, R. The Journal of organic chemistry 1973, 38, 3745-3749. (c) Verma, S. M.; Prasad, R. The Journal of organic chemistry 1973, 38, 1004-1010. (d) Verma, S. M.; Rao, S. O.; K.O.P., S. Bulletin of Chemical Society of Japan 1974, 47. (e) Verma, S. M.; Sinha, K. O. P.; Rao, C. K. Canadian Journal of Chemistry 1974, 52, 2399-2402. (f) Verma, S. M.; Singh, R. M. Bulletin of Chemical Society of Japan 1978, 51.

(4) Korsch, B. H.; Riggs, N. V. Tetrahedron Letters 1966, 7, 5897-5903.

(5) Fletcher, J. R.; Sutherland, I. O. Journal of the Chemical Society D: Chemical Communications 1969, 706-708.

(6) Rosen, B. R.; Werner, E. W.; Oâ€™Brien, A. G.; Baran, P. S. Journal of the American Chemical Society 2014, 136, 5571-5574.

(7) Shen, Y.; Friestad, G. K. The Journal of organic chemistry 2002, 67, 6236-6239.

(8) (a) Hynes, J.; Doubleday, W. W.; Dyckman, A. J.; Godfrey, J. D.; Grosso, J. A.; Kiau, S.; Leftheris, K. The Journal of organic chemistry 2004, 69, 1368-1371. (b) Draghici, C., The University of Vermont, 2009.

(9) Kamiński, K.; Obniska, J. Bioorganic & Medicinal Chemistry 2008, 16, 4921-4931.

(10) Bourel, L.; Tartar, A.; Melnyk, P. Tetrahedron Letters 1996, 37, 4145-4148.

(11) Conley, N. R.; Hung, R. J.; Willson, C. G. The Journal of organic chemistry 2005, 70, 4553-4555.

(12) Abbas, C.; Pickaert, G.; Didierjean, C.; Grégoire, B. J.; Vanderesse, R. Tetrahedron Letters 2009, 50, 4158-4160.

(13) Brosse, N.; Pinto, M.-F.; Bodiguel, J.; Jamart-Grégoire, B. The Journal of organic chemistry 2001, 66, 2869-2873.

(14) (a) Chan, D. M. T. Tetrahedron Letters 1996, 37, 9013-9016. (b) Anderson, J. C.; Cubbon, R.; Harding, M.; James, D. S. Tetrahedron: Asymmetry 1998, 9, 3461-3490. (c) Lim, Y.-K.; Lee, K.-S.; Cho, C.-G. Organic Letters 2003, 5, 979-982. (d) TÅjubrik, O.; MÅgeorg, U.; Sillard, R.; Ragnarsson, U. Tetrahedron 2004, 60, 8363-8373. (e) Aoki, Y.; Saito, Y.; Sakamoto, T.; Kikugawa, Y. Synthetic Communications 2000, 30, 131-140.

(15) Trapp, O. Topics in current chemistry 2013, 341, 231-269.

(16) D'Acquarica, I.; Gasparrini, F.; Pierini, M.; Villani, C.; Zappia, G. Journal of Separation Science 2006, 29, 1508-1516.

(17) (a) Atkinson, R. S.; Judkins, B. D. Tetrahedron Letters 1979, 20, 4001-4002. (b) Atkinson, R. S.; Judkins, B. D.; Patwardhan, B. Journal of the Chemical Society, Perkin Transactions 2 1979, 1490-1495. (c) Atkinson, R. S.; Barker, E.; Price, C. J.; Russell, D. R. Journal of the Chemical Society, Chemical Communications 1994, 1159-1160.

(18) (a) Al-Sehemi, A. G.; Atkinson, R. S.; Fawcett, J.; Russell, D. R. Journal of the Chemical Society, Perkin Transactions 1 2000, 4413-4421. (b) Al-Sehemi, A. G.; Atkinson, R. S.; Fawcett, J.; Russell, D. R. Tetrahedron Letters 2000, 41, 2243-2246. (c) Al-Sehemi, A. G.; Atkinson, R. S.; Fawcett, J.; Russell, D. R. Tetrahedron Letters 2000, 41, 2239-2242. (d) Al-Sehemi, A. G.; Atkinson, R. S.; Fawcett, J.; Russell, D. R. Chemical communications 2000, 43-44. (e) Atkinson, R. S.; Draycott, R. D.; Hirst, D. J.; Parratt, M. J.; Raynham, T. M. Tetrahedron Letters 2002, 43, 2083-2085.

(19) Sunal, S. G.; Yabanoglu, S.; Yesilada, A.; Ucar, G. Journal of neural transmission 2007, 114, 717-719.

Example 3

Chloromethylation of Hydrazides.

Significant utility has been found in natural products having trihalomethyl or dichloromethyl groups, which has led to a need for developing methodologies that focus on chloromethylation. Acrylanilides possess an activated double bond that can undergo the thermal addition to di/tri/tetrachloromethane derivatives.[4] In all the cases the metal mediated radical addition to acrylanilides afforded the oxindole based products. Loh et. al. have used dichloromethane as both solvent and reactant for iron-catalyzed radical addition reaction with acrylanilides and the solvent addition to activated alkene under thermal conditions has been reported.[5] Within this study Applicants investigate visible light mediated metal free solvent addition to acrylanilides.

Figure 8:
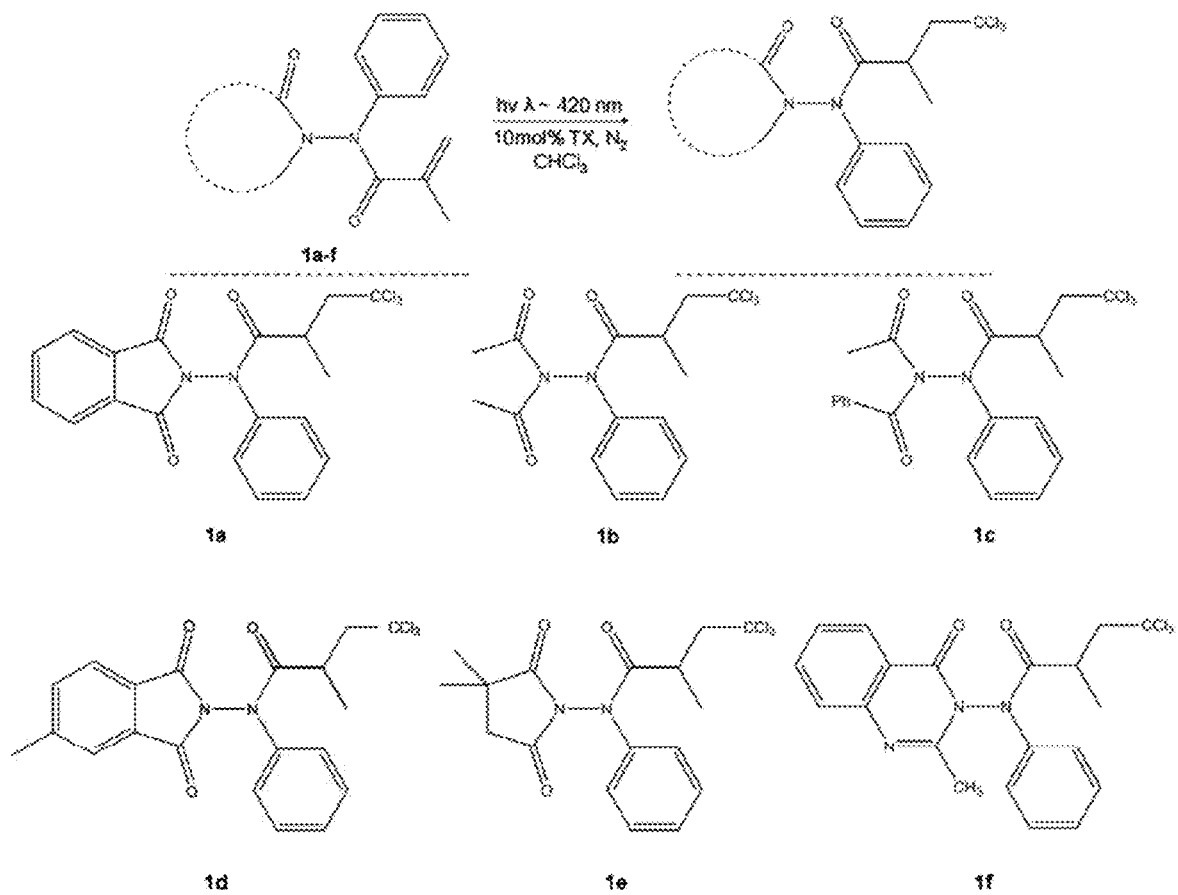
FIG. 8 shows metal free chloromethylation N—N bond based acrylanilides using visible light. (TX: thioxanthen-9-one, XRD structures provided for 1).
Figure 9:
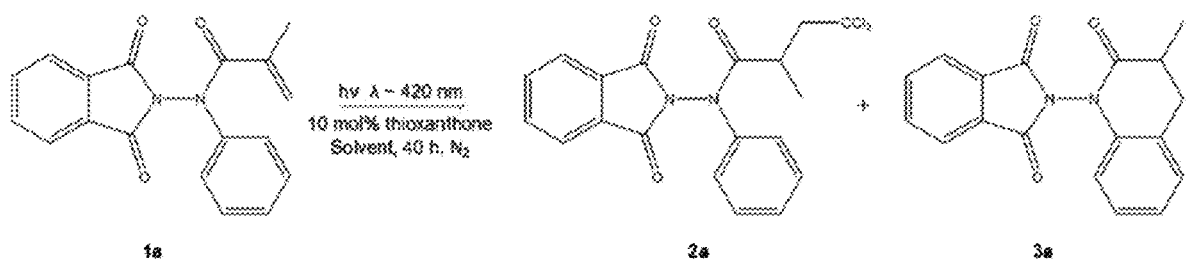
FIG. 9 shows intermolecular solvent photoaddition to acrylanilide derivative 1.
Figure 10:
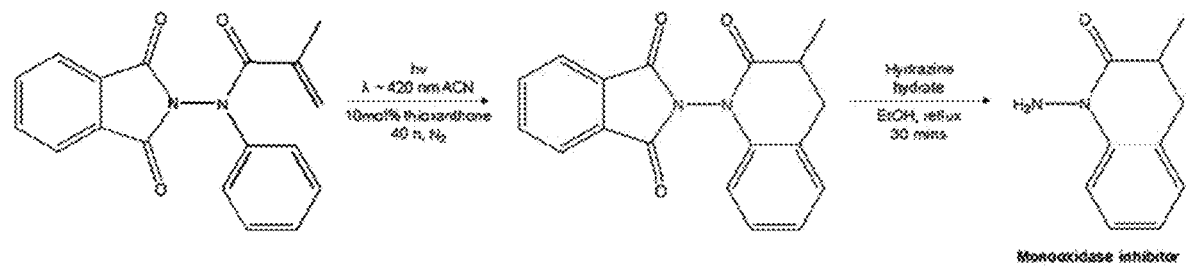
FIG. 10 shows the synthesis of biologically relevant molecules with an exemplary hydrazide based molecular template.
Figure 10:
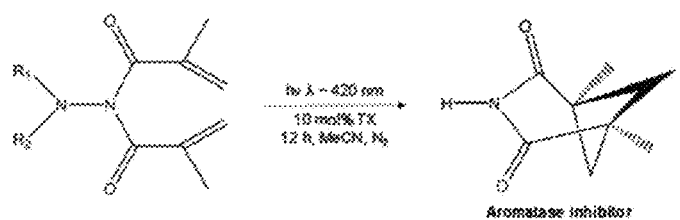
Figure 11:
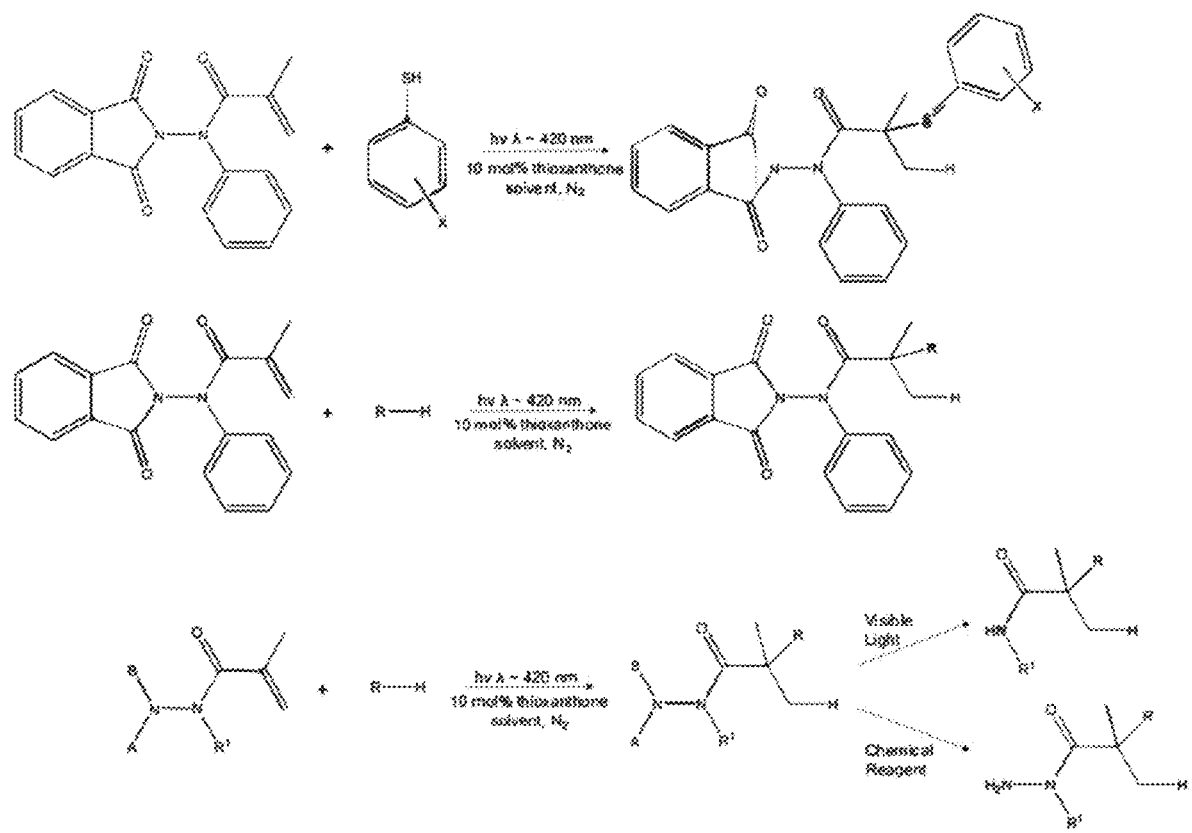
FIG. 11 shows the ligation and cleavage application in biological systems for tagging/clicking compounds and unclicking them using an exemplary hydrazide based molecular template.
Figure 12:
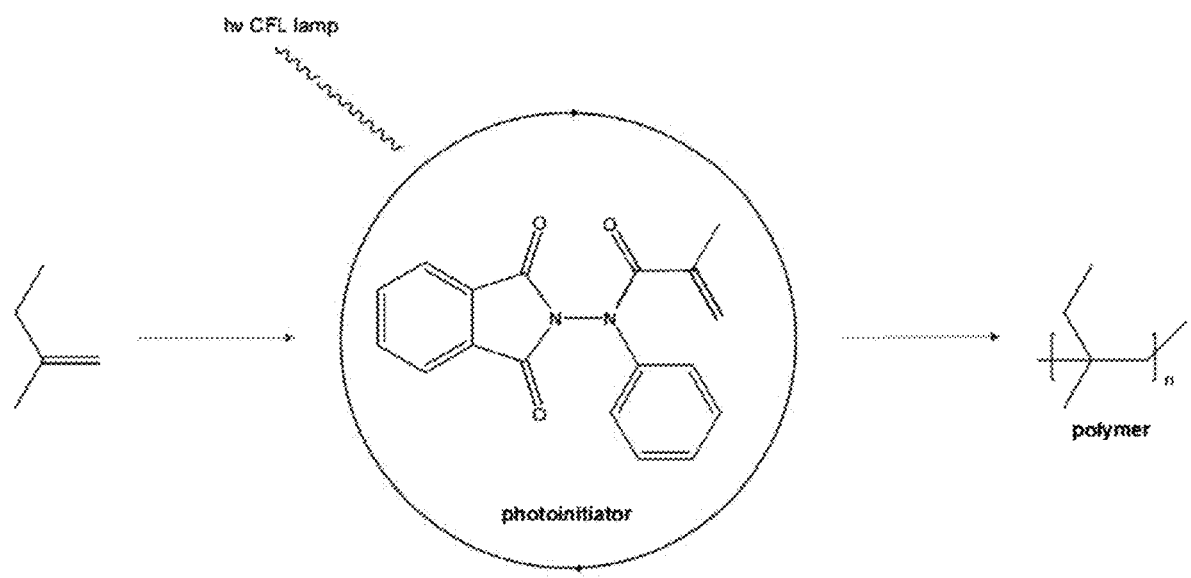
FIG. 12 shows the polymerization and materials synthesis with an exemplary hydrazide based molecular template.
Figure 13:
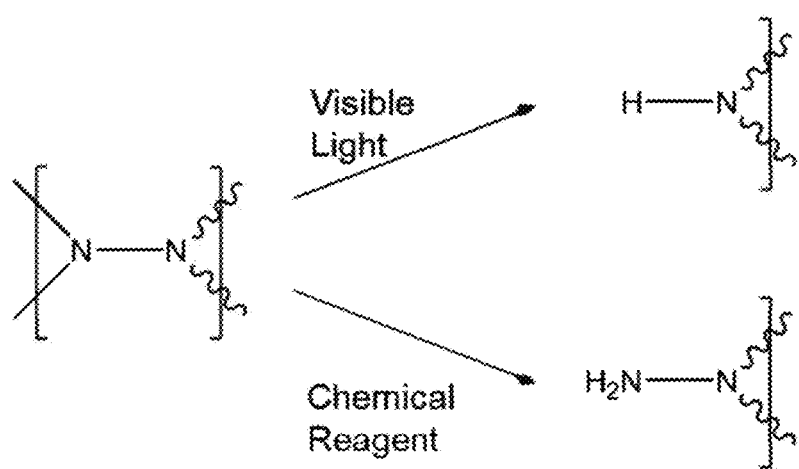
FIG. 13 shows the photodegradation of oligomers/polymers utilizing an exemplary hydrazide based molecular template.

Photoirradiation of 1a-f by visible light irradiation in the presence of thioxanthone in $CHCl_3$ led to facile of addition of the solvent across the double bond of the methacrolyl functionality (FIG. 8; Tables 6 and 7). The reaction was found to quite general for halogenated compounds (e.g. Solvents like $CH_2Cl_2$). The reaction was also efficient in deuterated solvents that showed deuterium incorporation in the product. Detailed studies were performed with 1a as the model system that showed that there is a competition between solvent addition and photocyclization. In solvents that had an activated hydrogen, solvent addition predominated (product 2a), while for solvents that do not have an active hydrogen, cyclization photoproduct 3a predominated.

TABLE 6

Visible light mediated Intermolecular $CHCl_3$ addition to hydrazides 1a-e

| Entry | Substrate[a] | Conversion/%[b] | dr[c] | t (h) |
|---|---|---|---|---|
| 1 | 1a | 100 | — | 40 |
| 2 | 1b | 50 | — | 11 |
| 3 | 1c | 44 | 1.5:1 | 11 |
| 4 | 1d | 93 | 2.1:1 | 8 |
| 5 | 1e | 46 | —* | 9 |

[a][1] = 3.26 mM, [2] = 3.84 mM, [3] = 3.10 mM, [4] = 3.12 mM, [5] =3.49 mM, [6] = 3.13 mM.
[b]Values based on $^1$H-NMR spectroscopy (±5% error), each experiment was performed for three trials, % conversion and mass balance calculated using triphenylmethane as internal standard.
[c]dr values are reporter based on crude $^1$H-NMR results.
*difficult to determine because of overlapping peaks.

Scheme 2: Intermolecular solvent photoaddition to acrylianilide derivative 1.

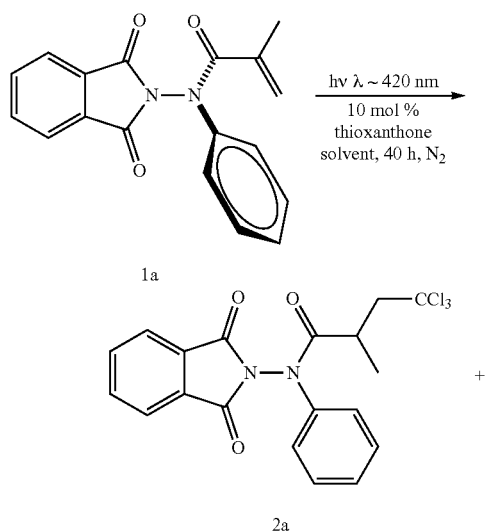

-continued

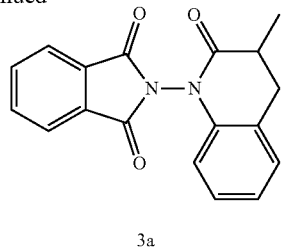

3a

TABLE 7

Summarized results for intermolecular photoaddition of chloromethanes to acryanilide derivative 1.

| Entry | Solvent[a] | Conversion.%[b] | 1a:1b[c] |
|---|---|---|---|
| 1 | $CCl_4$ | 100 | 1:>99 |
| 2 | $CHCl_3$ | 100 | >99:1 |
| 3 | $CDCl_3$ | 100 | 1:>99 |
| 4 | $CH_2Cl_2$ | 100 | 2.3:1 |
| 5 | $CD_2Cl_2$ | 96 | 1:>99 |

[a][1] = 3.26 mM.
[b]Values based on $^1$H-NMR spectroscopy (±5% error), each experiment was performed for three trials, % conversion and mass balance calculated using triphenylmethane as internal standard.
[c]values are reporter based on crude $^1$H-NMR results.
*difficult to determine because of overlapping peaks.

Example 4

Renewable and Sustainable Bio-Mass, Derived Photodegradable Polymers.

Figure 14:
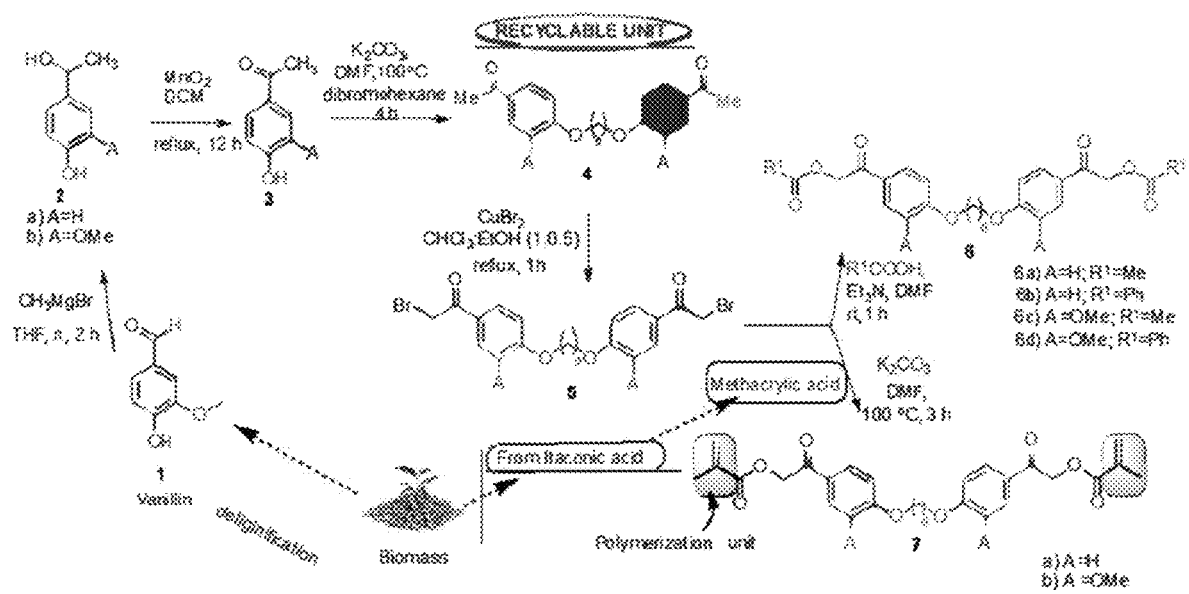
FIG. 14 shows a scheme for synthesis of exemplary bio-based polymers.

We envisioned to synthesis polymer (FIG. 14) with phenacyl as backbone (e.g. Biomass derivative viz., Vanillin 1) and bio-based methacrylic acid (which is a obtained from itaconic acid).[7]

Materials:

4-hydroxy acetophenone, Cupric bromide, Manganese dioxide, methacrylic acid, Chloroform, absolute ethanol, dry tetra hydrofuran, vanillin, dry dichloromethane was purchased from Alfa Aesar. Dibromo hexane, methyl magnesium bromide, triethyl amine were purchased form Sigma Aldrich.

Equipment:

NMR spectrometer: 1H-NMR and 13C-NMR spectra were recorded on Varian 500 MHz (125 MHz for 13C) or Bruker 400 MHz (100 MHz for 13C). Absorbance measurements: Agilent® Cary 300 UV-Vis spectrophotometer. Polymer molecular weights were measured using Gel Permeation Chromatography (GPC) with THE as an eluting solvent and at a flow rate of 0.35 mL/min on a Waters Modular system equipped with a refractive Index detector. The system utilized a TSKge; SupermultiporeHZ-M*2 column calibrated with polystyrene standards. The photoreaction was performed with Rayonet reactor hv ~350 nm. The compounds were purified by combiflash equipped with dual wavelength UV-Vis absorbance detector (Teledyn ISCO) using hexanes: ethyl acetate as the mobile phase and Redisep® cartridge filled with silica gel as stationary phase.

Methods:

Synthesis of Alcohol Derivative 2:

Vanillin 1 (1 equiv) was in a two-neck round bottom flask equipped with a stir bar. The flask was vacuumed and refilled with $N_2$ three times. THF was added through syringe and needle to dissolve the compound. 2.5 equiv. of Methyl magnesium bromide (in THF) was added to the reaction mixture and was stirred at room temperature for 2 hours. The progress of the reaction was monitored by TLC. After the reaction was finished $NH_4Cl$ solution was added to quench the reaction and extracted with ethyl acetate. The crude mixture was washed with brine solution and the organic layer was dried over $Na_2SO_4$. The crude compound was purified by column chromatography using ethyl acetate and hexane mixtures.

Synthesis of 3 by $MnO_2$ Oxidation:

Vanillin derivative (1 equiv) 2 was dissolved in dichloromethane and to this $MnO_2$ (6 equiv) was added and refluxed for 12 h. The crude compound is filtered through celite bed to remove undissolved manganese products. The crude reaction mixture was concentrated under reduced pressure and purified by column chromatography.

Synthesis of Phenacyl Dimer Derivative 4:

Hydroxyacetophenone derivative 3 (1 equiv) was taken in a round-bottomed flask and DMF was added. To this solution $K_2CO_3$ (2 equiv) was added, the color of the solution turned yellow, the solution was stirred and then 1,6 dibromohexane (0.5 equiv) was added. The reaction mixture was then refluxed at 100° C. and after 4 h the reaction was completed. The mixture was poured on crushed ice, pale white precipitate of product 4 was formed and was filtered under vacuum and washed with cold methanol (excess).

Synthesis of Phenacyl Bromo Derivative 5:

Compound 4 (1equiv) was dissolved in $CHCl_3$:Abs·EtOH (1:0.5 ratio) and to this $CuBr_2$ (6 equiv) was added. The reaction mixture was refluxed for 1 h and then filtered through celite bed to remove copper salt. The crude sample was concentrated under reduced pressure and then washed with methanol resulted in pale or white colored precipitate.

Synthesis of Phenacyl Ester Derivative 6:

Bromo phenacyl derivative 5 (1 equiv) was dissolved in acetonitrile/DMF under $N_2$ atmosphere. To this reaction mixture, triethyl amine (5 equiv) was added and stirred for 15 minutes at room temperature. Carboxylic acid (4 equiv) was added to the reaction mixture and stirred for 1 h. After the reaction was completed, water was added and organic layer was extracted with ethyl acetate. The organic layer was washed with saturated sodium bicarbonate solution and aqueous layer was drained. The separated organic layer was dried over $Na_2SO_4$. The compound was purified by column chromatography.

Synthesis of Methacrylate Derivative 7

Bromo phenacyl derivative 5 (1 equiv) was dissolved in DMF under $N_2$ atmosphere. To this reaction mixture, $K_2CO_3$ (5 equiv) and methacrylic acid (4 equiv) was added to the reaction mixture and refluxed for 3 h. After the reaction was completed, water was added and organic layer was extracted with diethyl ether. The organic layer was washed with saturated sodium bicarbonate solution and aqueous layer was drained. The separated organic layer was dried over $Na_2SO_4$. The compound was purified by column chromatography.

Figure 15:
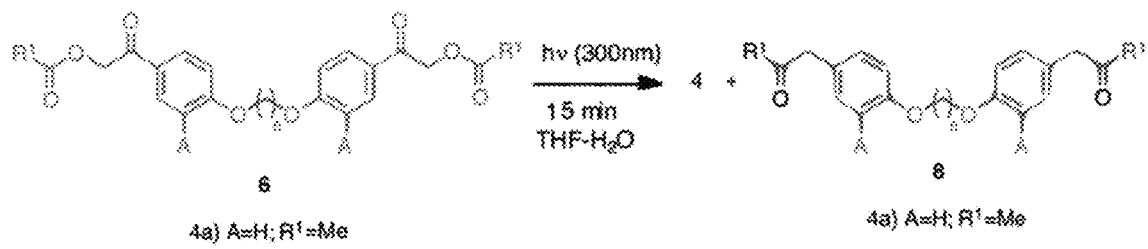
FIG. 15 shows a scheme for the photoreaction of phenacyl model system 6
Figure 16:
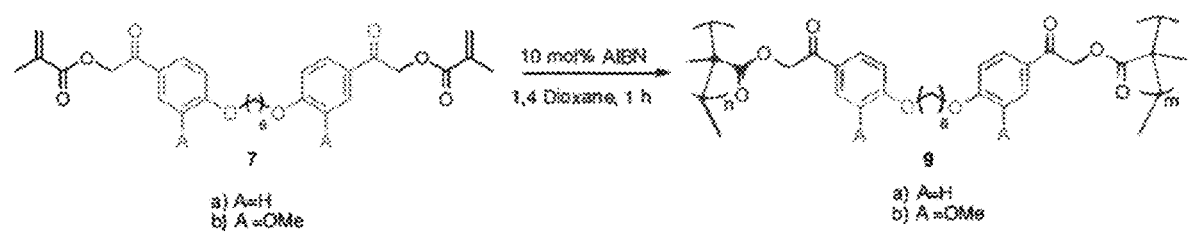
FIG. 16 shows a scheme for the polymerization of bio-based methacrylate derivative 7.
Figure 17:
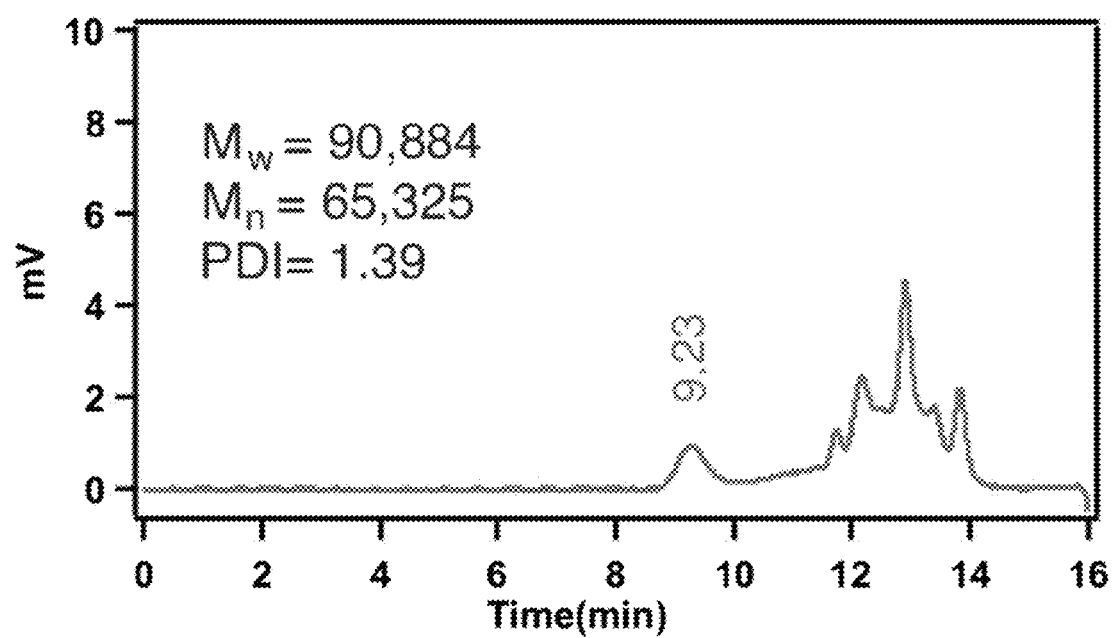
FIG. 17 shows GPC data for polymer 9, GPC analysis showed the mixture of polymer (Mw=90884, Mn=65,325 and PDI=1.4) and monomeric units.

We began our investigation with the model system with acetate as leaving group. Phenacyl model system was synthesized by reaction of 3 with dibromohexane in the presence of a base followed by bromination and coupling with the carboxylic acid derivatives yields ester derivatives. Irradiation of the ester 6 was carried out in Rayonet reactor equipped with 300 nm bulbs (16 lamps×14 watts each). The progress of the reaction was monitored by $^1$H-NMR analysis. We observed the formation of 4 and rearranged product 8, which presents an avenue to recycle the intermediate and use it in the preparation of polymer. With this success, we went ahead and worked on synthesizing polymer as reported in FIG. 15 with phenacyl trigger (to establish reaction conditions) and with the vanillin trigger (to showcase the use of biomass derived compounds for programmed degradation and recovery.

Monomer 7 was synthesized from the bromophenacyl derivative 5 in presence of base and methacrylic acid. Radical polymerization of the monomer was carried out in presence of AIBN for 1 h. After 1 h the polymer 9 was crashed out by addition of methanol to the reaction mixture. The insoluble product was filtered and washed with excess of methanol. Polymer 9 was not readily soluble in most of the organic solvents; therefore, in order to record the GPC, the partially soluble polymer was sonicated in THF for 1 h. The solution was filtered and the filtrate was analyzed by GPC.

Figure 18:
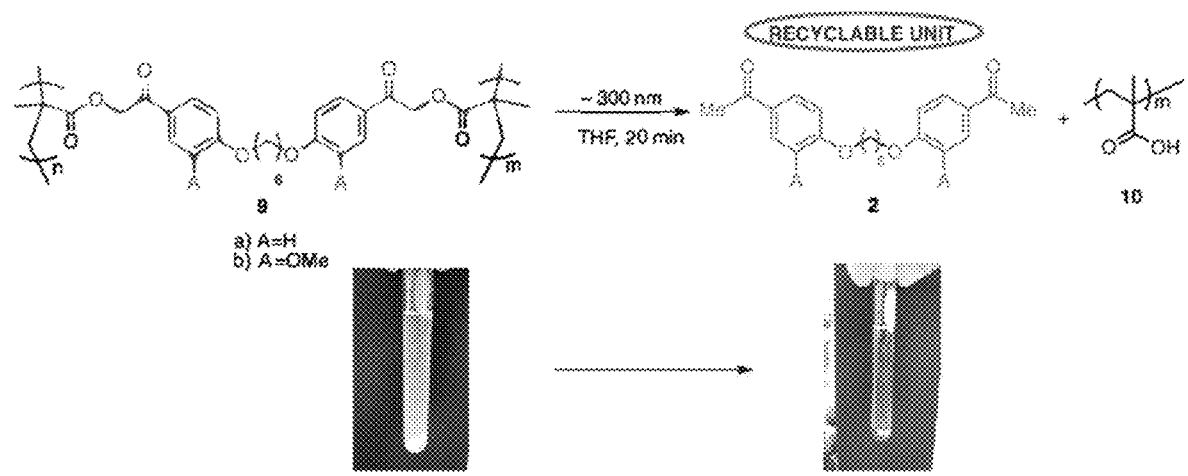
FIG. 18 shows a scheme for the photodegradation of polymer 9.

Photoreaction of the polymer was carried out as suspension in THE as shown in the picture. The photodegradation was completed in 20 min as the solution become clear indicating the complete cleavage. The formation of the ketone derivative was confirmed by 1H NMR analysis of crude reaction mixture. With the successful degradation of polymer derived from phenacyl derivative 7a, we develop a polymeric system 7b where the phototrigger is derived from biomass. The structural similarity between vanillin and p-hydroxy acetophenone (basic component of p-hydroxyphenacyl phototrigger) proved to be an excellent choice for renewable phototrigger source. Vanillin is one of the products obtained from delignification of woody biomass. We synthesized vanillin based model system and characterized by spectroscopic techniques. In order to understand the nature of the excited state we did preliminary photophysical experiments. On comparing the absorbance of vanillin and vanillin model system FIG. 18 (at same concentration and solvent) shows that the two-vanillin chromophore units in the molecule behave independently. Solvatochromic (Hyperchromic shift) studies show red shift for the peak around 315 nm with increasing polarity indicating a $\pi\pi^*$ nature of the excited singlet state.

No fluorescence was observed for vanillin 1 and vanillin model system 8 in non-polar solvents and polar aprotic solvents. A weak fluorescence was observed for vanillin model system in polar protic solvents. The absence of room temperature fluorescence indicates an efficient intersystem crossing to the triplet state, which was confirmed with the phosphorescence spectrum recorded for the model system. The absence of interaction between the two vanillin chromophore units in the model systems as evidenced from the absorbance and phosphorescence spectra was desired for it to be used as photo cleavable moiety. The triplet energy of the model system was estimated to be ~64 kcal/mol.

Figure 19:
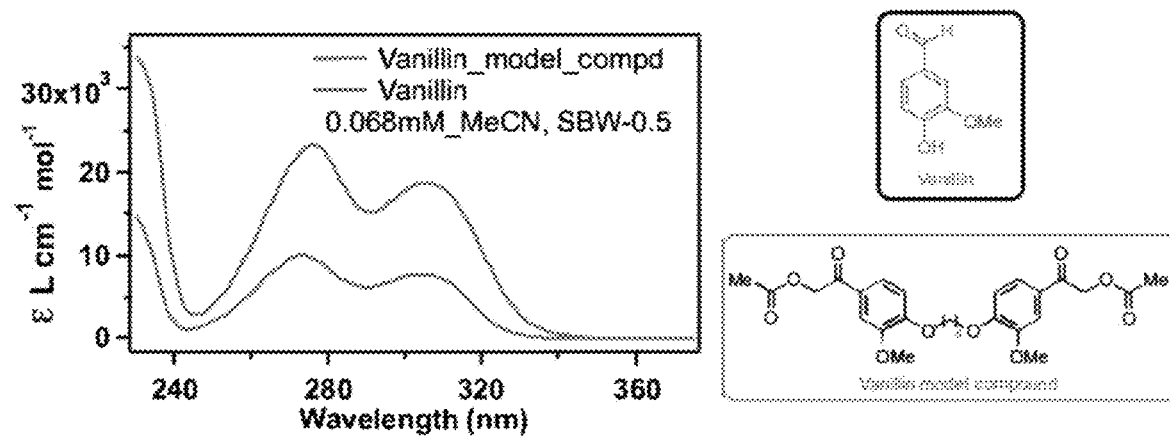
FIG. 19 shows the absorbance of vanillin and the vanillin model system.
Figure 20:
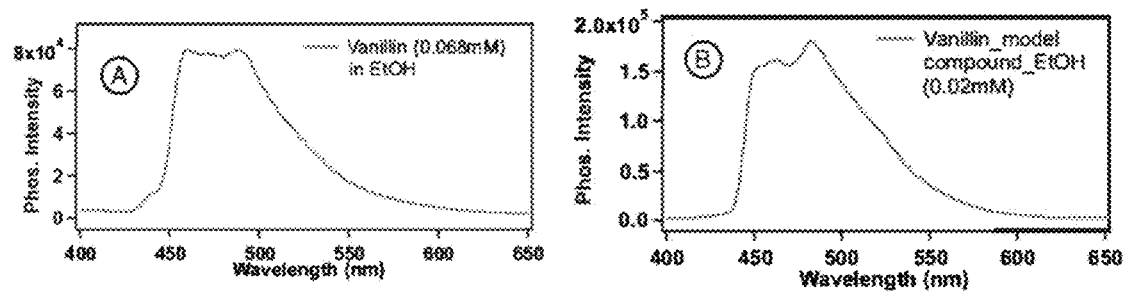
FIG. 20 shows the phosphorescence of vanillin (3A) and the vanillin model system (3B).

We have showcased the use of vanillin-based trigger than can be degraded with good efficiency around 300 nm (FIG. 19 and FIG. 20).

References (1) a) van Putten, R.-J.; van der Waal, J. C.; de Jong, E.; Rasrendra, C. B.; Heeres, H. J.; de Vries, J. G. *Chem. Rev.* 2013, 113, 1499-1597; b) Besson, M.; Gallezot, P.; Pinel, C. *Chem. Rev.* 2013, 114, 1827-1870; c) Auvergne, R.; Caillol, S.; David, G.; Boutevin, B.; Pascault, J.-P. *Chem. Rev.* 2013, 114, 1082-1115; d) Rosatella, A. A.; Simeonov, S. P.; Frade, R. F. M.; Afonso, C. A. M. *Green Chemistry* 2011, 13, 754-793; e) Moreau, C.; Belgacem, M.; Gandini, A. *Top. Catal.* 2004, 27, 11-30; f) Yao, K.; Tang, C. *Macromolecules* 2013, 46, 1689-1712.

(2) a) Gandini, A.; Silvestre, A. J. D.; Neto, C. P.; Sousa, A. F.; Gomes, M. *J. Polym. Sci., Part A: Polym. Chem.* 2009, 47, 295-298; b) Gomes, M.; Gandini, A.; Silvestre, A. J. D.; Reis, B. *J. Polym. Sci., Part A: Polym. Chem.* 2011, 49, 3759-3768.
(3) Rajendran, S.; Raghunathan, R.; Hevus, I.; Krishnan, R.; Ugrinov, A.; Sibi, M. P.; Webster, D. C.; Sivaguru, J. *Angew. Chem. Int. Ed.* 2015, 54, 1159-1163.
(4) Il'ichev, Y. V.; Schwörer, M. A.; Wirz, J. *J. Am. Chem. Soc.* 2004, 126, 4581-4595.
(5) Givens, R. S.; Rubina, M.; Wirz, J. *Photochem. Photobiol. Sci.* 2012, 11, 472-488.
(6) Anderson, J. C.; Reese, C. B. *Tetrahedron. Lett.* 1962, 3, 1-4.
(7) Harmsen, P. H., M. *Green building blocks for biobased plastics*.

Example 5

Figure 21:
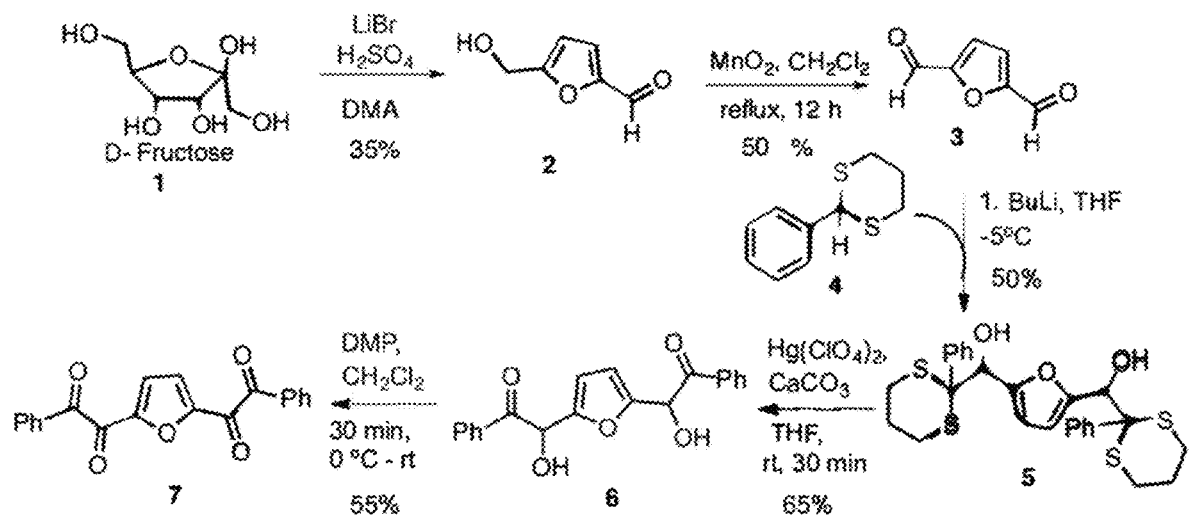
FIG. 21 shows the exemplary synthesis of photoinitiators from D-glucose.
Figure 22:
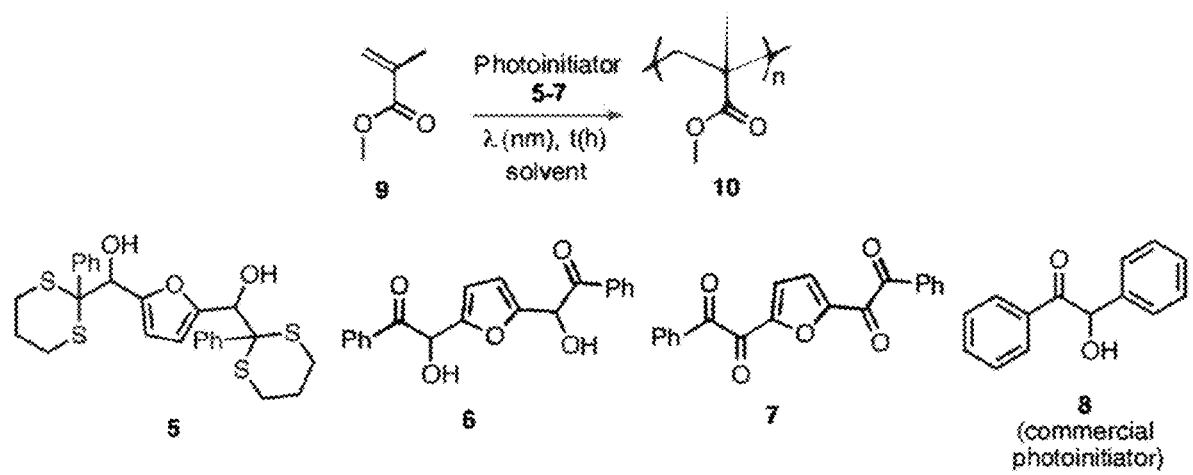
FIG. 22 shows polymerization of the photoinitiators generated in FIG. 22.
Figure 23:
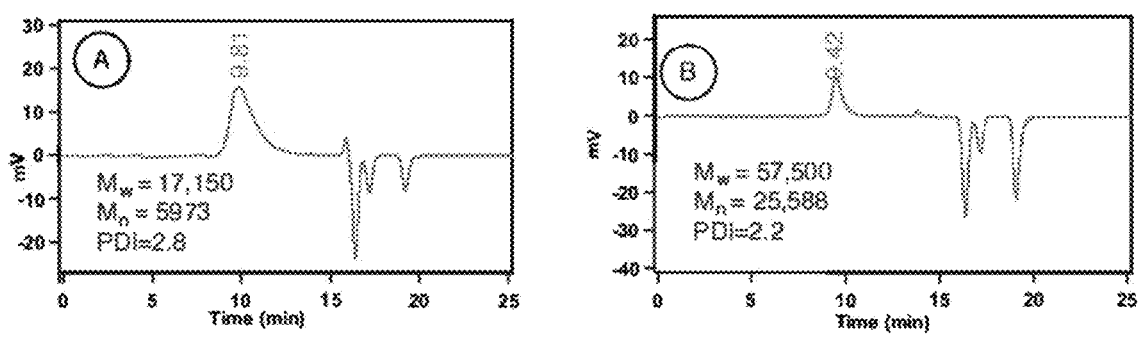
FIG. 23 shows GPC analysis of the methyl methacrylate (PMMA) photopolymerization with initiator 6 (left) and 7 (right).
Figure 24:
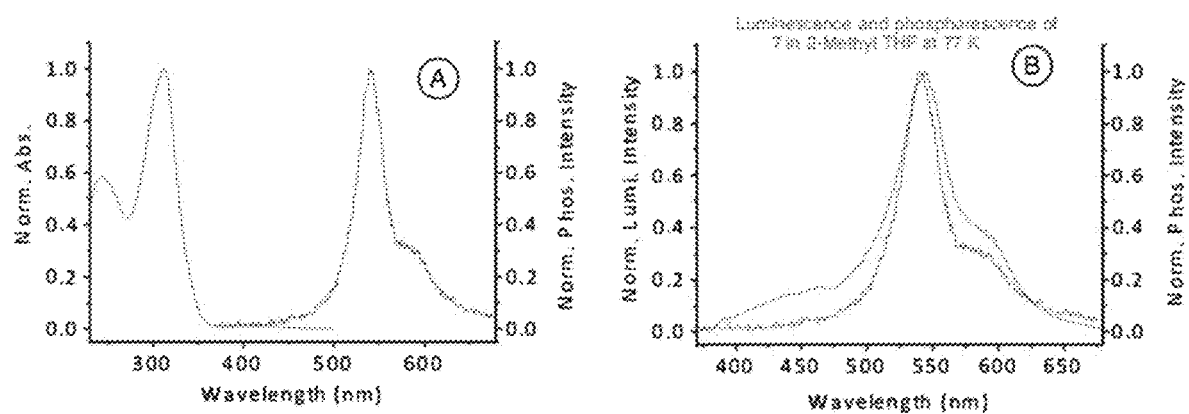
FIG. 24 shows the Absorption and Emission spectra (left) of 7 in 2-methyltetrahydrofuran at room temperature. Luminescence and phosphorescence spectra at 77 K (right).
Figure 25:
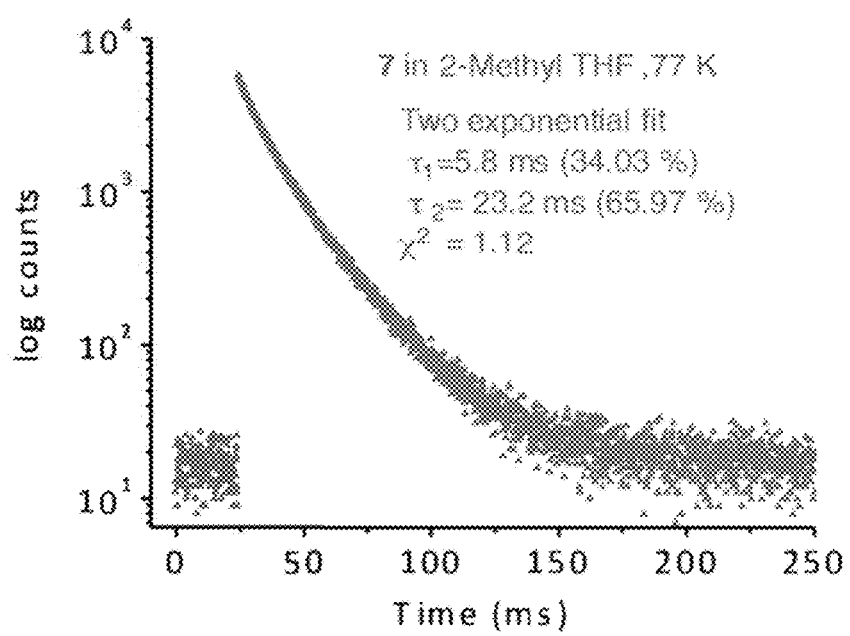
FIG. 25 shows phosphorescence lifetimes at 77K.
Figure 26:
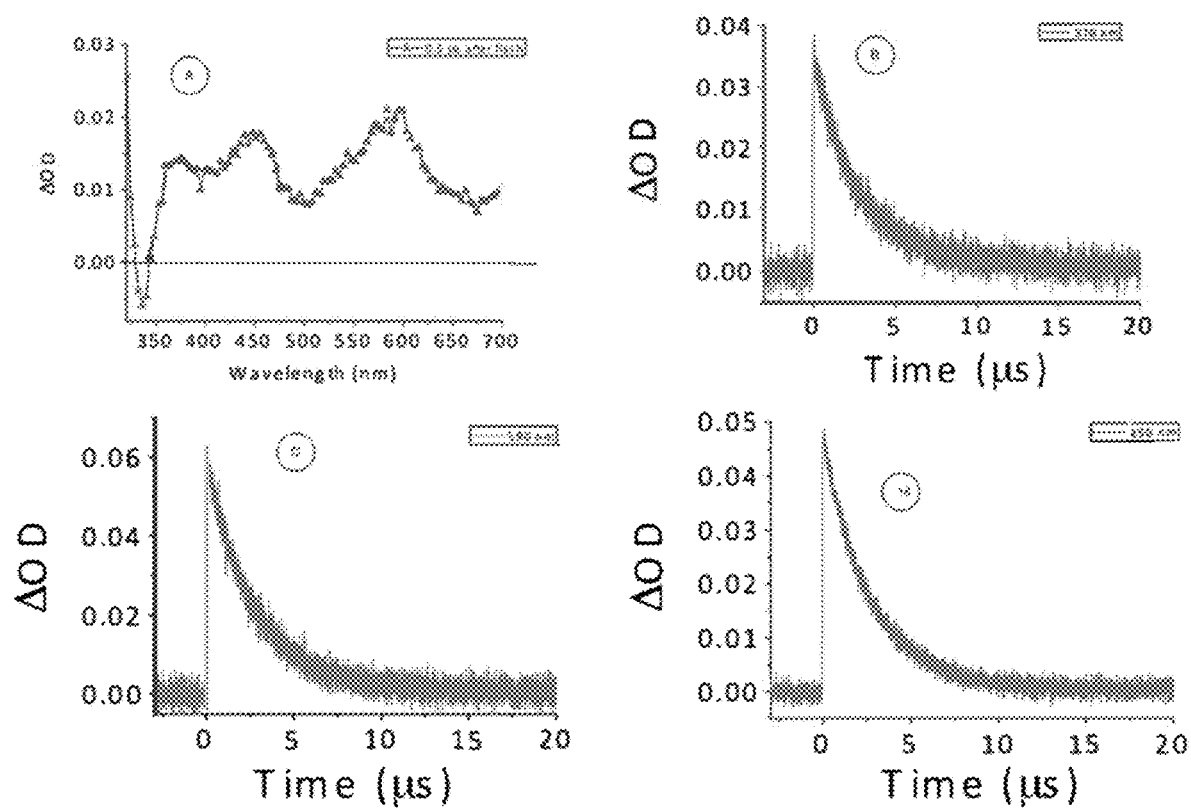
FIG. 26 shows the transient absorption kinetics observed at 370 nm (Top, Right), 450 nm (Bottom, Left), and 590 nm (Bottom, Right).

Biomass Derived Photoinitiators for the Synthesis of a Broad Spectrum of Polymers Using UV and/or Visible Light
Type-I Biomass Based Photoinitiators
Materials and Methods:
N, N-dimethylacetamide, n-butyl lithium, benzaldehyde was purchased form Sigma Aldrich. Manganese dioxide, D-fructose, Calcium carbonate, Dessmartin periodinane, Mercury perchlorate hydrate, Methyl methacrylate, methacrylate, dry Dichloromethane, dry Tetra hydrofuran, Acetonitrile were purchased from Alfa Aesar.
Equipment:
NMR spectrometer: 1H-NMR and 13C-NMR spectra were recorded on Varian 500 MHz (125 MHz for 13C) or Bruker 400 MHZ (100 MHz for 13C). Absorbance measurements: Agilent® Cary 300 UV-Vis spectrophotometer. Polymer molecular weights were measured using Gel Permeation Chromatography (GPC) with THE as an eluting solvent and at a flow rate of 0.35 mL/min on a Waters Modular system equipped with a refractive Index detector. The system utilized a TSKge; SupermultiporeHZ-M*2 column calibrated with polystyrene standards. The photoreaction was performed with Rayonet reactor hv ~350 nm. The compounds were purified by combiflash equipped with dual wavelength UV-Vis absorbance detector (Teledyn ISCO) using hexanes: ethyl acetate as the mobile phase and Redisep® cartridge filled with silica gel as stationary phase We developed biomass-derived photoinitiators starting from 5-hydroxy methyl furfural (HMF), one of the top 14-biobased chemicals as per the US department of energy.[2a] The present study details the development of type I photoinitiators 5-7 and compared their efficiency with well-established free radical initiator viz., Benzoin 8 (FIG. 23). Photoinitiators 5-7 were synthesized from D-glucose 1 as detailed in FIG. 21. Dehydration of D-fructose 1 using established conditions in literature led to HMF 2. HMF 2 was converted to di-aldehyde derivative 3 by $MnO_2$ oxidation. The diol 5 was synthesized by the reaction of 3 with dithiane protected Benzaldehyde 4. Dithiane deprotection of 5 yielded the bis-keto-alcohol 6, which upon Dess-Martin periodinane oxidation led to bis-dikteto 7. Due to the structural similarities, 5-7 we investigated all the three compounds for their ability to initiate photopolymerization and compared their efficiency with benzoin 8 (FIG. 22).

Free radical polymerization reaction of methyl methacrylate 9 leading to polymer 10 was taken as a model reaction to compare the efficiency of bio-based photo-initiators 5-7 with commercially available photo-initiator 8. To have a comparative study of the efficiency of the photoinitiators the optical density values were matched at irradiation wavelength (350 nm) and the photo-polymerization were carried out under identical conditions using a Rayonet reactor equipped with 16×12 W bulbs with a maximum output around 350 nm. After the photo-polymerization reaction, the polymer was characterized by $^1$H-NMR that was in good agreement with literature. We then analyzed the polymer by GPC and the comparison of Mw and PDI of the polymers are provided in Table 8.

Results and Discussion

Inspection of Table 1 shows that the bio-based photo-initiator 7 gave Mw of ~57,000 with a PDI of 2.2 compared to benzoin 8 that gave Mw of ~22,000 with a PDI of 4.8. This indicated that the biomass derived 7 was performing much better as a photo-initiator than commercially employed benzoin 8.

TABLE 8

Photopolymerization of methyl methacrylate with photo7initiators.[a]

| Entry | Photoinitiator | Solvent | λ (nm) | $M_W^d$ | PDI |
|---|---|---|---|---|---|
| 1 | 5 | $CH_2Cl_2$ | 300 | | |
| 2 | 6 | $CH_3CN$ | 350 | 17,150 | 2.8 |
| 3 | 7 | $CH_3CN$ | 350 | 57,500 | 2.2 |
| 4 | Benzoin | $CH_3CN$ | 350 | 22,150 | 4.8 |

[a] The photopolymerization were performed with rayonet reactor for 30 min under ambient conditions,. The molecular weights were measured using gel permeation chromatography (GPC) with THF as an eluting solvent and at a flow rate of 0.35 mL/min on a Waters Modular system equipped with a refractive Index detector. The system utilized a TSKge; SupermultiporeHZ-M*2 column calibrated with polystyrene standards.

Photophysical investigations (FIGS. 24-27) were carried out in order to gain more insight into the excited states of photoinitiator 7 and to understand the mechanism associated with photo-initiation process. The absorption of the molecule was recorded and the concentration was so adjusted that at 350 nm the optical density is ~0.1. This solution was used for fluorescence measurement. There was no fluorescence at room temperature indicating that the singlet-excited state was too short lived. The luminescence and phosphorescence spectra of the molecule indicated that the quenching of excited singlet was due to efficient ISC to the triplet. The nature of the triplet was found to be mostly nπ* with a slight ππ* mixing from the lifetimes recorded for phosphorescence. As the triplet of the molecule was populated relatively easy as shown by the fluorescence and phosphorescence experiments, it can be safely assumed that the reaction is from the lowest triplet of 7. The figure shows the various photophysical studies conducted for molecule 7.

Nano second transient absorption spectra (FIG. 27) were recorded using the third harmonic of Nd YAG as the excitation source. The nTA spectrum shows three major peaks centered around 370 nm, 450 nm and 590 nm. The lifetimes of all three decays were similar and was 2.7 μs.

Figure 27:
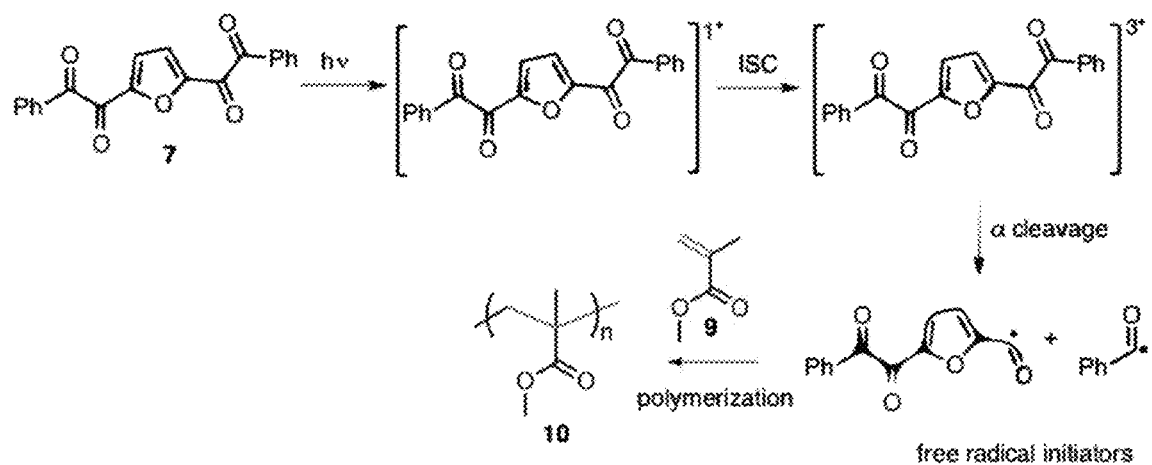
FIG. 27 shows proposed polymerization of photoinitiator 7.

Based on our photophysical experiments we believe that upon excitation the photoinitiator 7 it forms a singlet excited state species which then undergoes efficient intersystem crossing (ISC) forming a triplet state. The triplet-excited species undergoes a-cleavage generating two radical fragments, which initiates the polymerization (FIG. 27).

Our study showcases the use of simple transformations of biomass to develop photoinitiators that are efficiency in promoting polymerization. The development of green and sustainable strategies to synthesize high performance materials will minimize the stress on fossil fuels.

Type-II Bio-Based Derived Vanillin Photoinitiators
Materials and Methods:
All commercially obtained reagents/solvents were used as received; chemicals were purchased from Alfa Aesar®, Sigma-Aldrich®, Acros Organics®, TCI America®, Mallinckrodt®, and Oakwood® Products, and were used as received without further purification. Spectrophotometric grade solvents (ethanol and methylcyclohexanes) were purchased from Sigma-Aldrich® and used without further purification for emission measurements. Unless stated otherwise, reactions were conducted in oven-dried glassware under nitrogen atmosphere. $^1$H-NMR and $^{13}$C-NMR spectra were recorded on Varian 400 MHz (100 MHz for $^{13}$C) and on 500 MHz (125 MHz for $^{13}$C) spectrometers. Data from the $^1$H-NMR spectroscopy are reported as chemical shift (δ ppm) with the corresponding integration values. Coupling constants (J) are reported in hertz (Hz). Standard abbreviations indicating multiplicity were used as follows: s (singlet), b (broad), d (doublet), t (triplet), q (quartet), m (multiplet) and virt (virtual). Data for $^{13}$C NMR spectra are reported in terms of chemical shift (δ ppm).

Photophysical Methods.

Spectrophotometric solvents (Sigma-Aldrich®) were used whenever necessary unless or otherwise mentioned. UV quality fluorimeter cells (with range until 190 nm) were purchased from Luzchem®. Absorbance measurements were performed using a Shimadzu® UV-2501PC UV-Vis spectrophotometer. Emission spectra were recorded on a Horiba Scientific® Fluorolog 3 spectrometer (FL3-22) equipped with double-grating monochromators, dual lamp housing containing a 450-watt CW xenon lamp and a UV xenon flash lamp (FL-1040), Fluorohub/MCA/MCS electronics and R928 PMT detector. Emission and excitation spectra were corrected in all the cases for source intensity (lamp and grating) and emission spectral response (detector and grating) by standard instrument correction provided in the instrument software. Fluorescence emission spectra were processed by FluorEssence® software. Fluorescence lifetimes were determined by time correlated single photon counting using a pulsed diode (NanoLED) emitting at 263 nm and processed using DAS6® V6.4 software. The goodness-of-fit was assessed by minimizing the reduced chi squared function and further judged by the symmetrical distribution of the residuals.

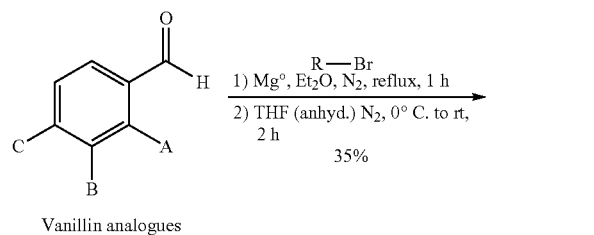

Vanillin analogues

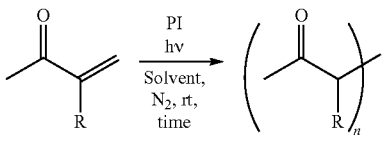

1a-1d

1a: R = Me; A = H; B = OMe; C = OH
1b: R = Me; A = H; B = OH; C = OMe
1c: R = Me; A = OH; B = OMe; C = H
1d: R = Ph; A = OH; B = OMe; C = H

To a solution of vanillin analogue in ether (anyd.) under N$_2$ atmosphere, the freshly prepared Grignard reagent was added at 0° C. After the starting material was consumed the reaction was quenched, extracted, separated, dried and concentrated then purified to yield the secondary alcohol.

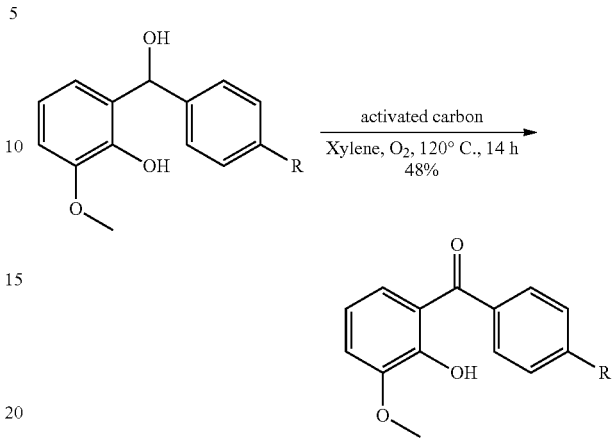

The secondary alcohol was dissolved in xylene (anhyd.) under O$_2$ atmosphere, followed by the addition of activated carbon. The mixture was allowed to stir at 120° C. for 14 hours before being filtered, dried, concentrated and purified to yield the benzophenone derivative.

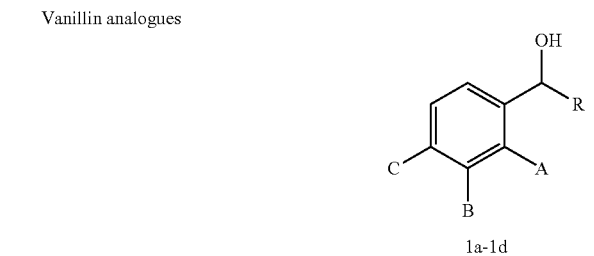

The photoinitiator (PI), and monomer were dissolved in organic solvent then purged with N$_2$. After purging the reaction mixture was irradiated with the desired light source. After polymer formation was noticed, the solvent was removed and the polymer analyzed.

Herein we report the synthesis of vanillin derived biobased initiators for visible light mediated photochemical polymerization instead of the traditional UV light mediated polymerization-involving benzophenone. Methylacrylate was chosen as the representative monomer for polymerization. The polymerization efficiency of benzophenone derivatives were compared to that of benzophenone. Various co-initiators were evaluated and the extent of photoinitiator excited state quenching will be investigated, corroborating photochemistry and photophysical data.

Figure 28:
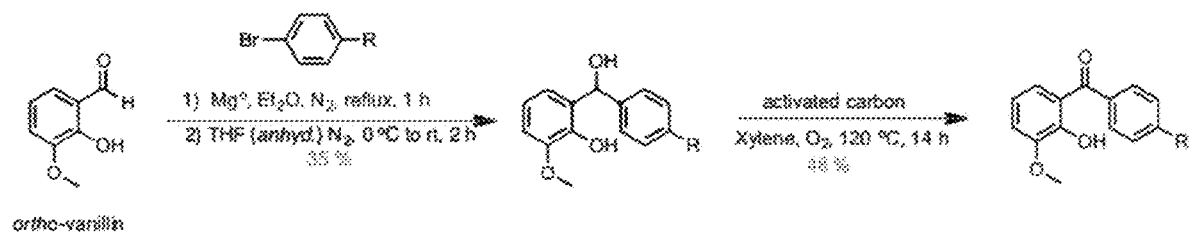
FIG. 28 shows the proposed scheme for the synthesis of benzophenone photo-initiators.

Benzophenone derivatives were synthesized from ortho-vanillin in two easy steps according to FIG. 28. The structures of photoinitiators were confirmed by 1H NMR, 13C NMR, and HRMS spectroscopy. Photophysical measurements were taken for the photoinitiators.

Figure 29:
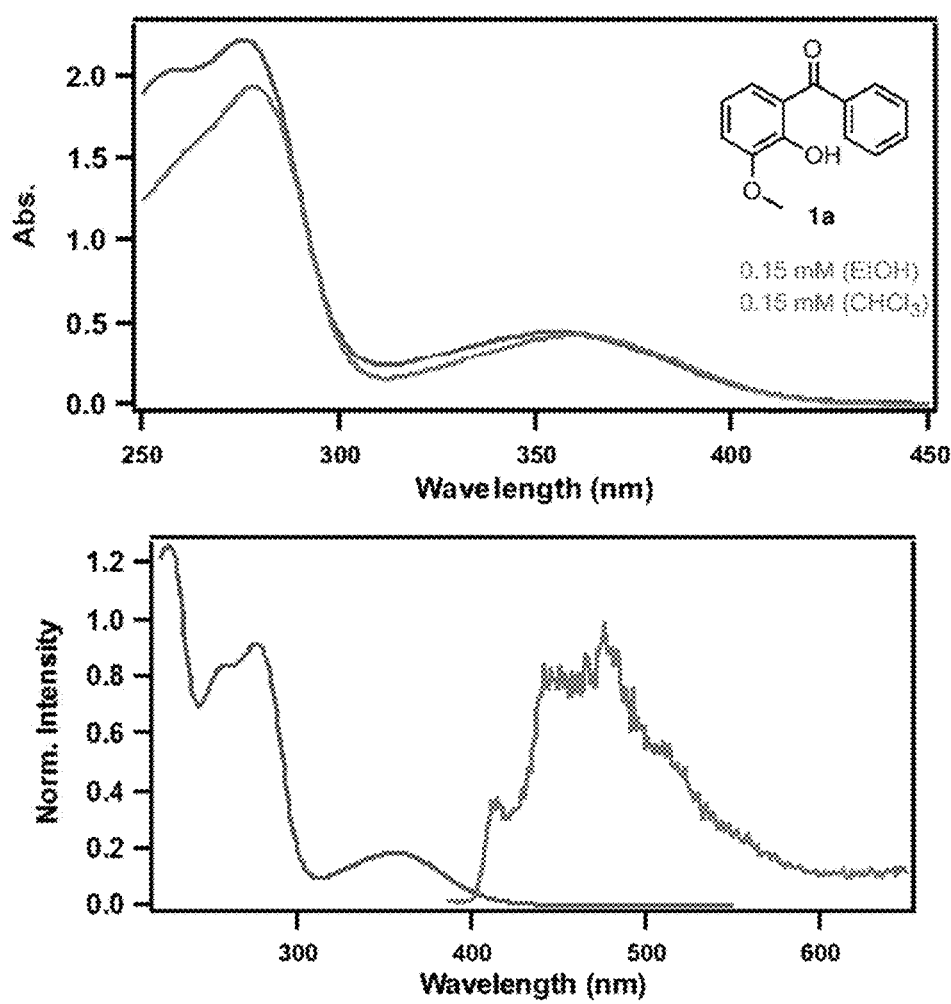
FIG. 29 shows Absorbance spectra in various solvents (Top), Absorbance (blue) and phosphorescence (red) at 77 K in EtOH (Bottom). λexc 385 nm, OD.@λexc=0.35, λem 400 nm to 750 nm.

Results and Discussion: Table 9 lists properties of the benzophenone photoinitiators. FIG. 29 displays the absorbance spectra of the photoinitiator. It can be seen in FIG. 29 that the substitution of the benzophenone derivatives causes a bathochromic shift in the absorbance with respect to that of benzophenone (BP). The overlap of the phosphorescence spectra indicates a small singlet triplet gap (E$_{ST}$). A hypsochromic shift from less polar solvent CHCl$_3$ to more polar solvent EtOH can be noticed in the absorbance spectra (FIG. 29). As mentioned above, benzophenone is a Type-II photoinitiator thus light irradiation excites benzophenone, and its appropriately substituted derivatives, to the singlet excited state and due to inter-system crossing its triplet excited state is populated. Inter-system crossing occurs near unity efficiency in benzophenone due to spin orbit coupling of the excited singlet and triplet states (5b). The triplet excited state of benzophenone is $n\pi^*$ in character (5b). H-abstraction is more efficient from the $n\pi^*$ triplet excited state. Thus, the $n\pi^*$ triplet state is of prime importance in Type-II photochemical polymerization reactions. Literature supports that substitution can change the triplet excited state character of benzophenone derivatives as seen in Michler's ketone composed of $\pi\pi^*$ triplet excited state (5b). Phosphorescence spectra were taken in efforts to determine the triplet energy and triplet state configuration of benzophenone derivatives (Table 9 and FIG. 30).

TABLE 9

Photophysical parameters with vanillin derived photoinitiators

| Photoinitiator | $\lambda_{max}$ (nm) | $\lambda_{onset}$ (nm) | $E_T$ (kcal/mol) | $\tau_T$ (msec) |
|---|---|---|---|---|
| 1a | 354 | ~415 | 69.6 | |
| BP[a] | 340 | ~375 | 70.2 | 6.2 |

From Reference 2b

After confirming $n\pi^*$ triplet state with photophysical data, namely phosphorescence lifetimes polymerization reactions with methacrylate as the monomer in the presence of various co-initiators was investigated (Table 2). Both electron transfer co-initiators were employed and H-abstraction co-initiators (entry 5, entries 1-2). It can be seen that only thiophenol affords the desired polymer with a Mw of 157 k and a PDI 1.9. Table 10 displays preliminary photochemical polymerization data.

TABLE 10

Polymerization

| entry | photo-initiator | co-initiator | t/h[g] | $M_w$ (g/mol) | PDI |
|---|---|---|---|---|---|
| 1[f] | BP | ndea | 1 | —[a] | —[a] |
| 2[e] | BP | thiophenol | 1 | —[a] | [a] |
| 3[e] | 1a | — | 4 | na[b] | na[b] |
| 4[f] | 1a | ndea | 4 | na[b] | na[b] |
| 5[e] | 1a | tea | 4 | na[b] | na[b] |
| 6[f] | 1a | thiophenol | 4 | 157,848 | 1.9 |
| 7[e] | 1a | cysteine | 4 | na[b] | na[b] |
| 8[e] | 1a | thiophenol | 1 | —[a] | —[a] |

[a]Data needs to still be determined. 1 H NMR spectroscopy displays polymer formation.
[b]no polymer noticed via 1 H NMR spectroscopy.
[c]NDEA = n-ethyl diethanolamine;
[d]TEA = triethylamine.
[e]trials 2,3,5,7-8 reactions performed in MeCN as the solvent.
[f]entries 1,4,6 reactions performed in CHCl3;
[g]All reactions irradiated at 350 nm in rayonet reactor.
[h]pLED employed for irradiation spectral distribution centered at 400 + 5 nm.

Type-III Biobased Photoacids
Results and Discussion:

Investigations commenced determining the extent or existence of excited state proton transfer, photoacidity (pKa*), of vanillin and its analogs ortho-vanillin and iso-vanillin. From the Foster cycle, pKa* is mathematically defined by the following equation, $$pk_a^* = pK_a + (E_{A-} - E_{HA})/2.3RT.^1 \quad (1)$$

Figure 32:
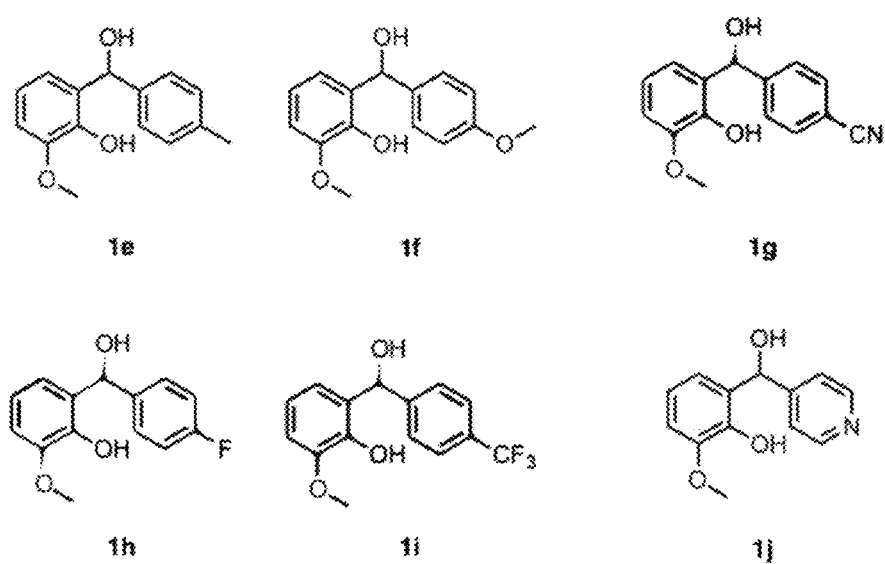
FIG. 32 shows the substrate scope of vanillin photoacids.
Figure 33:
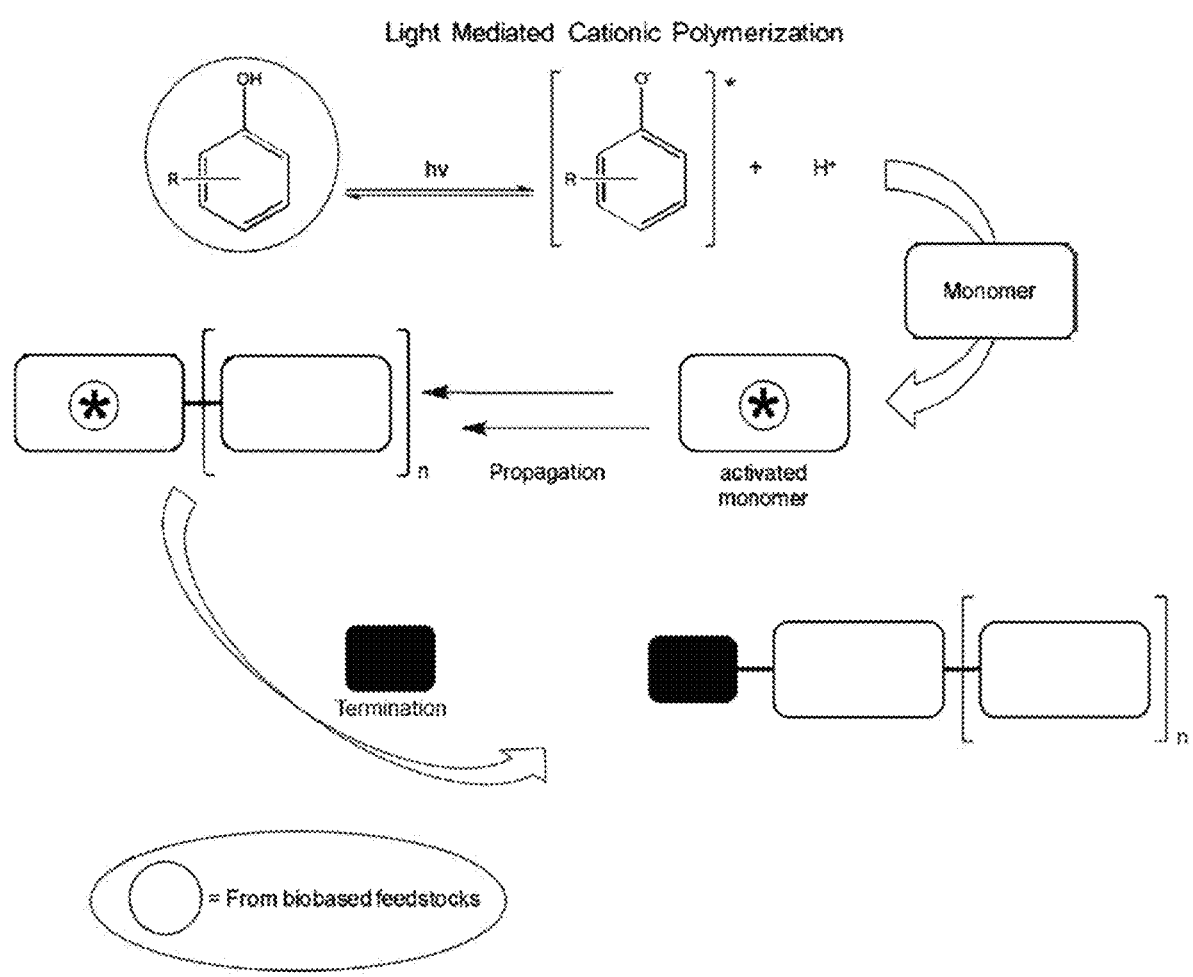
FIG. 33 shows the Light Mediated Cationic Polymerization.

Thus pKa* is most commonly calculated from the difference in the Si excited state 0-0 transition of the acid ($E_{HA}$) and the conjugate base ($E_{A-}$) (2c). In order to determine the excited state acidity of the vanillin analogs, the ground state acidity was determined. An a-plot was made, by taking the UV-Vis spectra of ortho-vanillin at various pH using NaOH and HCl as the base and acid respectively (5c). Both iso-vanillin and vanillin ground state acidities were literature reported. After obtaining the ground state acidity the excited state acidity (pKa*) was investigated. Fluorescence, phosphorescence and luminescence spectra were measured in different solvents. It was determined that none of the vanillin analogs fluoresced appreciably and therefore were all poor photoacids. Vanillin and its analogs displayed respectable phosphorescence indicating that photons were lost by way of inter-system crossing to the triplet excited state. Various substituted Grignard reagents were used to reduce the carbonyl to a tertiary alcohol therefore eliminating the carbonyl functionality and hindering inter-system crossing (FIG. 32).

Figure 30:
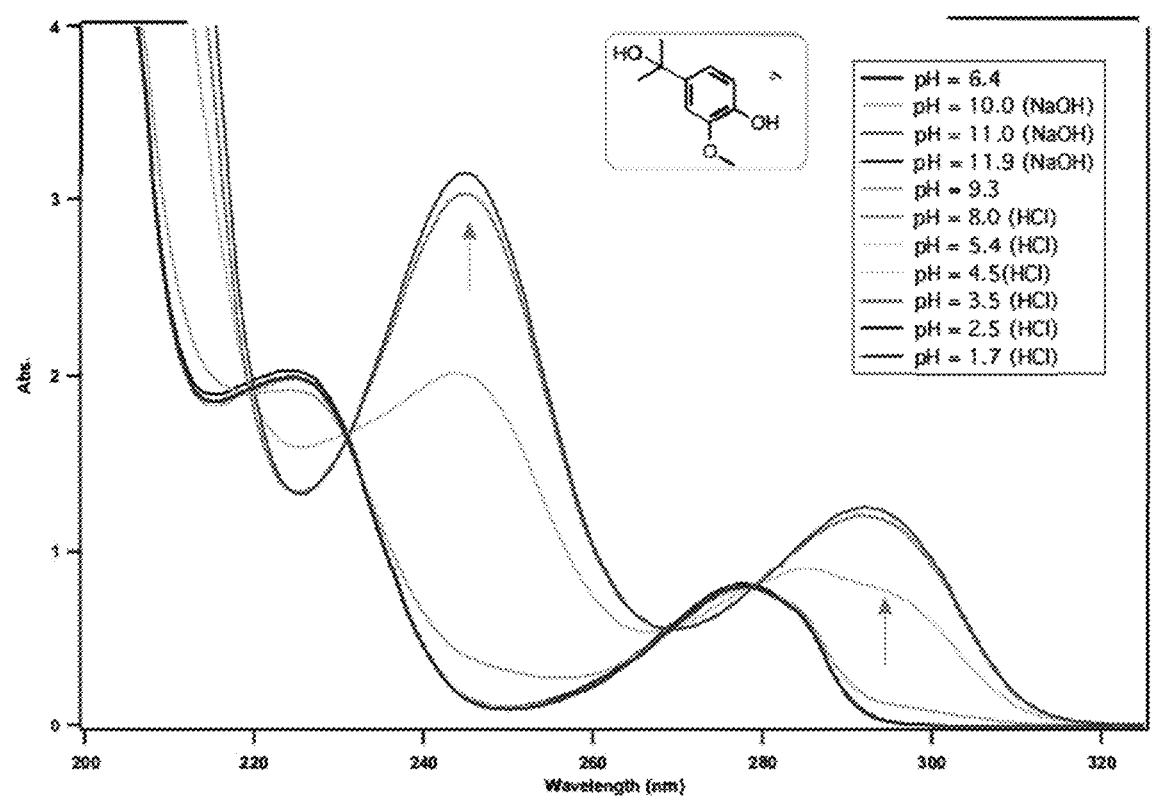
FIG. 30 shows the Absorbance at various pH in HPLC water.
Figure 31:
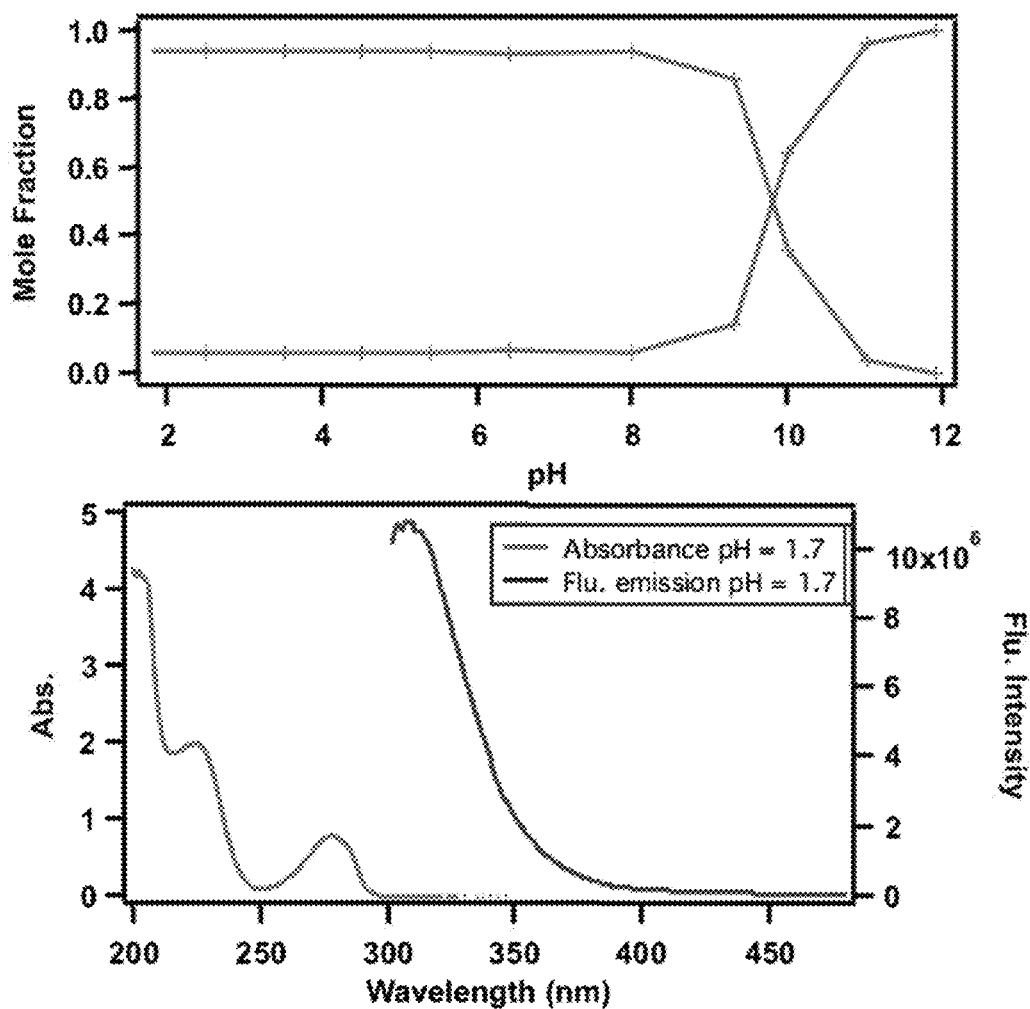
FIG. 31 shows the a-plot (top), acidic absorbance (bottom) in aqueous solution (red) and emission (green).

The ground state and excited state acidities were determined. FIG. 30 displays representative spectra necessary to determine both ground and excited state acidities (Table 11). It was determined that the methyl Grignard adduct of ortho-vanillin 1c, was more acidic in the excited state (pKa*=4.9). Derivatives 1a and 1b were handled in a similar fashion. Table 11 displays the excited state energies of 1a-1d and their corresponding photoacidity.

TABLE 11

Excited States and Photoacidity of Vanillin Derived Photoacids

| Entry | Cmpd | pKa | pKa* | EO⁻ (nm) | EOH (nm) |
|---|---|---|---|---|---|
| 1 | 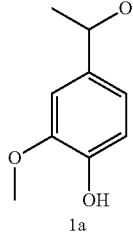 1a | 9.8 | 9.6 | 304 | 303 |
| 2 | 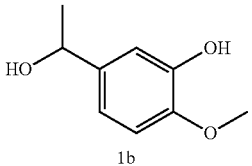 1b | 9.8 | 5.6 | 303 | 285 |
| 3 | 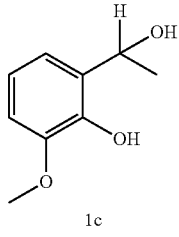 1c | 8 | 4.9 | 315 | 301 |

TABLE 11-continued

Excited States and Photoacidity of Vanillin Derived Photoacids

| Entry | Cmpd | pKa | pKa* | EO⁻ (nm) | EOH (nm) |
|---|---|---|---|---|---|
| 4 | 1d | | | | |

Upon inspection of Table 11 the relevance of positional substitution on the aromatic ring can be easily noticed. However, it is more difficult to notice the relevance of the secondary substitution (R-group) upon photoacidity. In efforts to better comprehend the influence of secondary substitution on the photoacidity substrates 1e-1j will be synthesized and their photoacidity evaluated. Lastly, in efforts to display the utility of vanillin based photoacids cationic polymerization will also be attempted (FIG. 32).

REFERENCES

1a. Tehfe, A. M.; Louradour, F.; Lalevée, J.; Fouassier, J.-P., Photopolymerization Reactions: On the Way to a Green and Sustainable Chemistry. Applied Sciences 2013, 3 (2).
2a. (a) van Putten, R.-J.; van der Waal, J. C.; de Jong, E.; Rasrendra, C. B.; Heeres, H. J.; de Vries, J. G., Hydroxymethylfurfural, A Versatile Platform Chemical Made from Renewable Resources. Chem. Rev. 2013, 113 (3), 1499-1597; (b) Besson, M.; Gallezot, P.; Pinel, C., Conversion of Biomass into Chemicals over Metal Catalysts. Chem. Rev. 2013, 114 (3), 1827-1870; (c) Auvergne, R.; Caillol, S.; David, G.; Boutevin, B.; Pascault, J.-P., Biobased Thermosetting Epoxy: Present and Future. Chem. Rev. 2013, 114 (2), 1082-1115; (d) Rosatella, A. A.; Simeonov, S. P.; Frade, R. F. M.; Afonso, C. A. M., 5-Hydroxymethylfurfural (HMF) as a building block platform: Biological properties, synthesis and synthetic applications. Green Chemistry 2011, 13 (4), 754-793.
1b) a) Chatani, S.; Kloxin, C.; Bowman, C., Polym. Chem., 2014, 5, 2187. b) Yang, J.; Shi, S.; Xu, F.; Nie, J., Photochem. Photobiol. Sci., 2013, 12, 323-329
2b Kumasaka, R.; Kikuchi, A.; Yagi, M., Photochem. and Photobio., 2014, 90, 727-733.
3b Schneider, L.F-J.; Cavalcante, L.; Consani, S.; Ferracane, J., Dental Materials, 2009, 25, 369-375.
4b Sudha, B.; Kamble, R.; Shashikanth, S., J. Serb. Chem. Soc., 2008, 73, 261-270
5b) Palit, D., Res. Chem. Intermd. 2005, 31, 205-225
6b) Barsotti, F.; Brigante, M.; Sarakha, M.; Maurino, V.; Minero, Vione, D., Photochem. Photobiol. Sci., 2015, 14, 2087-2096
1c The Chemistry of Phenols; Rappoport, Z.; John Wiley & Sons: Chicester, U. K., 2003
2c) aTolbert, L.; Solntsev, K., Acc. Chem. Res., 2002, 35, 19-27. b) Tolbert, L.; Haubrich, J., J. Am. Chem. Soc., 1994, 116, 10593-10600.
3c) Simkovitch, R.; Shomer, S.; Gepshtein, R.; Roth, M., J. Photochem. Photobiol., A, 2014, 277, 90-101
4c) a) Alvarez, T. M.; Russell, M. M.; Zink, J. I, Chem. Commun., 2014, 50, 8388-8390.
b) Keitz, B.; Grubbs, R., J. Am. Chem. Soc., 2009, 131, 2038-2039. c) Shirai, M.; Tsunooka, M., Bull. Chem. Soc. Jpn. 1998, 71, 2483-2507. d) Lishin, N.; Albertazzi, L.; Bendikov, M.; Baran, P.; Shabat, D., J. Am. Chem. Soc., 2012, 134, 20412-20420. e.) Iwata, R.; Uda, K.; Takahashi, D.; Toshima, K., Chem. Commun., 2014, 50, 10695-10698.
5c) Reijenga, J.; Hoof, A. v.; Loon, A. V.; Teunissen, B., Analytical Chem. Insights, 2013, 8, 53-71.
6c) Torti, E.; Giustina, D. Gioia, Protti, S.; Merli, D.; Brusatin, G.; Fagnoni, M., RSC Adv., 2015, 5, 33239-33248
7c) Bomgardner, M.,

What is claimed is:
1. A biomass derived, photodegradable polymer comprising:
at least one first monomeric unit derived from biomass, wherein the first monomeric unit is derived from lignin and comprises a methacrylate; and
at least one second monomeric unit derived from biomass comprising an arylmethyl, a benzoin, or a phenacyl phototrigger.
2. The photodegradable polymer of claim 1, further comprising at least one third monomeric unit, wherein the third monomeric unit is not derived from biomass.
3. The photodegradable polymer of claim 1, wherein the first monomeric unit is also a photoinitiator.
4. The photodegradable polymer of claim 1, wherein photocleavage of said polymer occurs from exposure to light from about 300 nm to about 450 nm in wavelength.
5. The photodegradable polymer of claim 1, wherein the second monomeric unit comprises a phenacyl phototrigger.
6. The photodegradable polymer of claim 1, wherein the first monomeric unit is derived from vanillin, ortho-vanillin, or iso-vanillin.
7. The photodegradable polymer of claim 1, wherein the first monomeric unit has the formula:

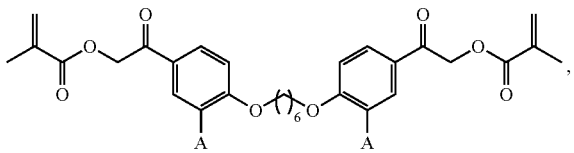

wherein A is H or Ome.
8. The photodegradable polymer of claim 1, wherein the photodegradable polymer comprises a greater number of first monomeric units than second monomeric units.
9. The photodegradable polymer of claim 2, wherein the photodegradable polymer comprises greater numbers of third monomeric units compared to the number of second monomeric units.
10. The photodegradable polymer of claim 1, wherein photodegradable polymer comprises a plurality of second monomeric units that photocleave at different wavelengths.
11. The photodegradable polymer of claim 2, wherein the third monomeric unit is obtained from a petroleum product or is chemically or enzymatically synthesized.
12. The photodegradable polymer of claim 2, wherein the third monomeric unit is a hydrophilic monomer.
13. The photodegradable polymer of claim 2, wherein the third monomeric unit comprises an alkylene glycol.

14. A method for recycling the photodegradable polymer of claim 1, the method comprising:
exposing the photodegradable polymer to light having a wavelength selected so as to cause photocleavage of the polymer to yield one or more recycled monomers or oligomers.

15. The method of claim 14, wherein the light is from about 300 nm to about 450 nm in wavelength.

16. The method of claim 14, wherein the recycled monomer or oligomer has the formula:

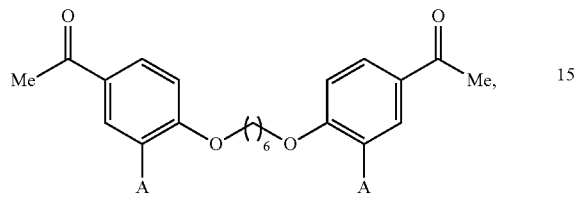

wherein A is H or OMe.

17. The method of claim 14, further comprising utilizing at least one of the recycled monomers or oligomers to synthesize a recycled polymer comprising the recycled monomer or oligomer.

* * * * *